(12) United States Patent
Van Gompel et al.

(10) Patent No.: US 6,217,563 B1
(45) Date of Patent: Apr. 17, 2001

(54) THREE-DIMENSIONAL, INWARD LEG GATHER DISPOSABLE GARMENT

(75) Inventors: Paul Theodore Van Gompel, Hortonville; Yung Hsiang Huang, Appleton, both of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/250,471

(22) Filed: Feb. 12, 1999

Related U.S. Application Data
(60) Provisional application No. 60/084,515, filed on May 7, 1998.

(51) Int. Cl.$^7$ ...................................................... A61F 13/20
(52) U.S. Cl. ..................................... 604/385.101; 604/378
(58) Field of Search ............................... 604/358, 385.01, 604/385.21, 385.22, 385.23, 385.28, 378, 386, 387, 385.101, 385.06

(56) References Cited

U.S. PATENT DOCUMENTS

| Re. 33,106 | 11/1989 | Beckestrom . |
|---|---|---|
| 3,776,233 | 12/1973 | Schaar . |
| 3,885,568 | 5/1975 | Schaar . |
| 3,901,236 | 8/1975 | Assarsson et al. . |
| 3,920,018 | 11/1975 | Schaar . |
| 3,978,861 | 9/1976 | Schaar . |
| 4,076,663 | 2/1978 | Masuda et al. . |
| 4,081,301 | 3/1978 | Buell . |

(List continued on next page.)

FOREIGN PATENT DOCUMENTS

| 0 669 855 | 6/1996 | (AU) . |
|---|---|---|
| 0 217 032 A3 | 4/1987 | (EP) . |
| 0 567 792 A1 | 11/1993 | (EP) . |
| 0 591 647 A2 | 4/1994 | (EP) . |
| 0 604 764 A1 | 7/1994 | (EP) . |

(List continued on next page.)

OTHER PUBLICATIONS

American Society for Testing Materials (ASTM) Designation: D 5169–91, "Standard Test Method for Shear Strength (Dynamic Method) of Hook and Loop Touch Fasteners," pp. 687–689, published Nov. 1991.

(List continued on next page.)

*Primary Examiner*—Anhthuan T. Nguyen
(74) *Attorney, Agent, or Firm*—Paul Yee

(57) ABSTRACT

An integral absorbent article, such as diaper (10), has a longitudinal article length (26) and a lateral article width (24). The article includes an absorbent composite (32) having first and second longitudinally opposed end regions (78) and (79), and at least a first longitudinally terminal end edge (82). The absorbent composite (32) includes a substantially liquid-impermeable backsheet layer (30), a substantially liquid permeable topsheet layer (28), and a retention portion (48) sandwiched between the backsheet and topsheet layers. The retention portion (48) has laterally opposed, terminal side edges (49), and the absorbent composite (32) includes a pair of laterally opposed side margins (80) which extend laterally beyond the side edges (49) of the retention portion (48). A first body panel (52) is joined to the first longitudinal end (78) of the absorbent composite (32). The first body panel (52) has a body side surface (54), an outward surface (56), a panel length (58) which is less than the article length (26), an outboard terminal end edge (60), and a relatively inboard terminal end edge (62). Each of the side margins (80) of the absorbent composite (32) is inwardly turned to provide a turned bodyside surface (100) and a turned outward side surface 102 of each side margin (80). At least a first portion of the turned bodyside surface (100) of each side margin (80) of the absorbent composite (32) is secured to the outward surface (56) of the first body panel (52) with a body panel attachment (42).

23 Claims, 10 Drawing Sheets

U.S. PATENT DOCUMENTS

| | | |
|---|---|---|
| 4,249,532 | 2/1981 | Polansky et al. . |
| 4,286,082 | 8/1981 | Tsubakimoto et al. . |
| 4,341,216 | 7/1982 | Obenour . |
| 4,534,769 | 8/1985 | De Jonckheere et al. . |
| 4,595,441 | 6/1986 | Holvoet et al. . |
| 4,663,220 | 5/1987 | Wisneski et al. . |
| 4,666,542 | 5/1987 | De Jonckheere . |
| 4,687,477 | 8/1987 | Suzuki et al. . |
| 4,699,620 | 10/1987 | Bernardin . |
| 4,699,823 | 10/1987 | Kellenberger et al. . |
| 4,701,172 | 10/1987 | Stevens . |
| 4,701,173 | 10/1987 | Zehner et al. . |
| 4,701,174 | 10/1987 | Johnson . |
| 4,701,175 | 10/1987 | Boland et al. . |
| 4,704,116 | 11/1987 | Enloe . |
| 4,710,187 | 12/1987 | Boland et al. . |
| 4,731,066 | 3/1988 | Korpman . |
| 4,738,677 | 4/1988 | Foreman . |
| 4,747,846 | 5/1988 | Boland et al. . |
| 4,753,646 | 6/1988 | Enloe . |
| 4,756,709 | 7/1988 | Stevens . |
| 4,762,582 | 8/1988 | de Jonckheere . |
| 4,834,738 | 5/1989 | Kielpikowski et al. . |
| 4,850,990 | 7/1989 | Huntoon et al. . |
| 4,883,480 | 11/1989 | Huffman et al. . |
| 4,916,005 | 4/1990 | Lippert et al. . |
| 4,936,840 | 6/1990 | Proxmire . |
| 4,938,753 | 7/1990 | Van Gompel et al. . |
| 4,938,754 | 7/1990 | Mesek . |
| 4,938,755 | 7/1990 | Foreman . |
| 4,950,262 | 8/1990 | Takagi . |
| 4,965,122 | 10/1990 | Morman . |
| 5,019,066 | 5/1991 | Freeland et al. . |
| 5,019,073 | 5/1991 | Roessler et al. . |
| 5,026,364 | 6/1991 | Robertson . |
| 5,034,007 | 7/1991 | Igaue et al. . |
| 5,037,416 | 8/1991 | Allen et al. . |
| 5,098,423 | 3/1992 | Pieniak et al. . |
| 5,133,707 | 7/1992 | Rogers et al. . |
| 5,226,992 | 7/1993 | Morman . |
| 5,263,948 | 11/1993 | Karami et al. . |
| 5,263,949 | 11/1993 | Karami et al. . |
| 5,269,775 | 12/1993 | Freeland et al. . |
| 5,304,159 | 4/1994 | Tanji et al. . |
| 5,360,422 | 11/1994 | Brownlee et al. . |
| 5,399,219 | 3/1995 | Roessler et al. . |
| 5,486,166 | 1/1996 | Bishop et al. . |
| 5,490,846 | 2/1996 | Ellis et al. . |
| 5,527,303 | 6/1996 | Milby, Jr. et al. . |
| 5,531,730 | 7/1996 | Dreier . |
| 5,540,671 | 7/1996 | Dreier . |
| 5,540,796 | 7/1996 | Fries . |
| 5,542,942 | 8/1996 | Kline et al. . |
| 5,558,660 | 9/1996 | Dreier . |
| 5,558,661 | 9/1996 | Roe et al. . |
| 5,562,650 | 10/1996 | Everett et al. . |
| 5,571,096 | 11/1996 | Dobrin et al. . |
| 5,580,411 | 12/1996 | Nease et al. . |
| 5,593,401 | 1/1997 | Sosalla et al. . |
| 5,595,618 | 1/1997 | Fries et al. . |
| 5,605,735 | 2/1997 | Zehner et al. . |
| 5,624,422 | 4/1997 | Allen . |
| 5,624,429 | 4/1997 | Long et al. . |
| 5,628,737 | 5/1997 | Dobrin et al. . |
| 5,643,242 | 7/1997 | Lavon et al. . |
| 5,836,932 | 11/1998 | Buell et al. . |
| 5,843,066 | 12/1998 | Dobrin . |
| 5,895,379 | 4/1999 | Litchholt et al. . |
| 5,897,547 | 4/1999 | Schmitz . |
| 5,947,948 | 9/1999 | Roe et al. . |
| B1 4,636,207 | 11/1989 | Buell . |
| B1 4,662,875 | 4/1989 | Hirotsu et al. . |

FOREIGN PATENT DOCUMENTS

| | | |
|---|---|---|
| 2 068 316 A1 | 2/1993 | (FR) . |
| 2 284 741 | 6/1996 | (GB) . |
| 2 297 474 | 8/1996 | (GB) . |
| 2 297 491 | 8/1996 | (GB) . |
| 8 402 274 | 2/1985 | (NL) . |
| WO 88/06008 A1 | 8/1988 | (WO) . |
| WO 93/03698 A1 | 3/1993 | (WO) . |
| WO 94/28844 A2 | 12/1994 | (WO) . |
| WO 95/02384 A1 | 1/1995 | (WO) . |
| WO 96/19166 A1 | 6/1996 | (WO) . |
| WO 96/22064 A1 | 7/1996 | (WO) . |
| WO 96/23466 A1 | 8/1996 | (WO) . |
| WO 96/31179 A2 | 10/1996 | (WO) . |
| WO 96/32083 A1 | 10/1996 | (WO) . |
| WO 97/00056 A1 | 1/1997 | (WO) . |
| WO 97/14385 A1 | 4/1997 | (WO) . |
| WO 97/24094 A1 | 7/1997 | (WO) . |
| WO 97/24283 A1 | 7/1997 | (WO) . |
| WO 97/26850 A1 | 7/1997 | (WO) . |
| WO 97/46185 A1 | 12/1997 | (WO) . |
| WO 98/33465 A1 | 8/1998 | (WO) . |
| 92/6027 | 8/1992 | (ZA) . |

OTHER PUBLICATIONS

American Society for Testing Materials (ASTM) Designation: D 5170–91, "Standard Test Method for Peel Strength ("T" Method) of Hook and Loop Touch Fasteners," pp. 690–692, published Nov. 1991.

American Society for Testing Materials (ASTM) Designation: D 882–95a, "Standard Test Method for Tensile Properties of Thin Plastic Sheeting," pp. 182–187, published Dec. 1995.

Federal Test Method Standard (FTMS) No. 191A, Method 5514, "Water Resistance of Cloth; Low Range, Hydrostatic Pressure Method," Jul. 20, 1978, 3 pages.

TAPPI Official Test Method T543 om–94, "Bending Resistance of Paper (Gurley Type Tester)," published by the TAPPI Press, Atlanta, Georgia, pp. 1–7.

THREE-DIMENSIONAL, INWARD LEG GATHER DISPOSABLE GARMENT

This application claims priority from presently copending U.S. Provisional Application No. 60/084,515 entitled "A Disposable Garment Having Dryness Barriers With Expandable Attachment To An Absorbent" and filed on May 7, 1998, in the name of Paul.

FIELD OF THE INVENTION

The present invention relates to garment articles. More particularly, the present invention relates to absorbent articles, desirably disposable absorbent articles, which are assembled and integrated to form a unitary structure.

BACKGROUND OF THE INVENTION

Conventional garment articles, such as disposable diapers and other disposable absorbent articles, have typically employed adhesive or mechanical fasteners which attach appointed waistband sections of the articles around a wearer. In addition, various configurations of waist elastics, leg elastics, elasticized liners, and elasticized outer covers have been employed on garment articles to help produce and maintain the fit of the articles about the body contours of the wearer.

The external surfaces of such disposable absorbent products may include a nonwoven fibrous material or a matte-finished film material. In some arrangements, pattern embossments have been formed into outward surface of the outer cover to provide a decorative pattern. Other disposable garments have had outer covers composed of elastomeric fabrics.

In particular configurations of disposable absorbent articles, inner elasticized waistband flaps have been incorporated along the bodyside surface of the article. The waistband, inner flap component can extend along a portion of the lateral width of the waistband section of the article, and may have a lateral extent which is equal to or greater than the lateral extent of the outer cover of the article.

In other configurations, the article may include an absorbent assembly attached to the inward surface of a relatively large waistband member. The waistband member is typically elasticized and disposed at one end of the absorbent assembly. The waistband member extends beyond the terminal edge of that end of the absorbent assembly, and also extends beyond the laterally opposed side edges of the absorbent assembly.

Conventional garment articles, such as those described above, have not provided desired levels of fit, absorbency, resistance to leakage, low cost and ease of manufacture. As a result, there has been a continued need for more effective garments having improved combinations of such properties.

BRIEF DESCRIPTION OF THE INVENTION

Generally stated, the present invention provides an absorbent article having a longitudinal article length and a lateral article width. The article includes an absorbent composite having longitudinally opposed end regions, and at least a first longitudinally terminal end edge. The absorbent composite includes a substantially liquid-impermeable backsheet layer, a substantially liquid permeable topsheet layer, and a retention portion sandwiched between the backsheet and topsheet layers. The retention portion has laterally opposed, terminal side edges, and the absorbent composite includes a pair of laterally opposed side margins which extend laterally beyond the side edges of the retention portion. A body panel is joined to a longitudinal end of the absorbent composite. The body panel has a body side surface, an outward surface, an outboard terminal end edge, and a relatively inboard terminal end edge. In particular aspects of the invention, each of the side margins of the absorbent composite can be inwardly turned to provide a turned bodyside surface and a turned outward side surface of each side margin. In additional aspects, at least a first portion of the turned bodyside surface of each side margin of the absorbent composite can be secured to the outward surface of the first body panel.

By incorporating its various aspects, the article of present invention can provide an article having improved fit, improved absorbency and improved resistance to leakage. The article can also be produced at lower cost and with greater efficiency. In particular, the expandable attachment sections which join the absorbent composite to the body panel can allow the absorbent composite to increase in volume during use while allowing the body panel to maintain a close and conforming fit around the waist and torso of the wearer's body. The body panel can also better provide a more effective barrier between the wet absorbent composite and the wearer's skin. Where elasticized legbands and expandable sections of the absorbent composite are located in the intermediate, crotch portion of the diaper, the expandable portion can also allow the absorbent composite to grow in volume substantially without affecting the fit of the elasticized legbands about the wearer's legs.

BRIEF DESCRIPTION OF THE DRAWINGS

The present invention will be more fully understood and further advantages will become apparent when reference is made to the following detailed description of the invention and the drawings, in which.

DETAILED DESCRIPTION OF THE INVENTION

The various aspects and embodiments of the invention will be described in the context of a disposable absorbent article, such as a disposable diaper. It is, however, readily apparent that the present invention could also be employed with other articles, such as feminine care articles, children's training pants, incontinence garments and the like. Typically, the disposable articles are intended for limited use and are not intended to be laundered or otherwise cleaned for reuse. A disposable diaper, for example, is discarded after it has become soiled by the wearer. Optionally, a disposable diaper may include a single-use, absorbent insert, and a limited-use outer cover which may be reused several times.

It should also be noted that, when employed in the present disclosure, the terms "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof.

Figure 1:
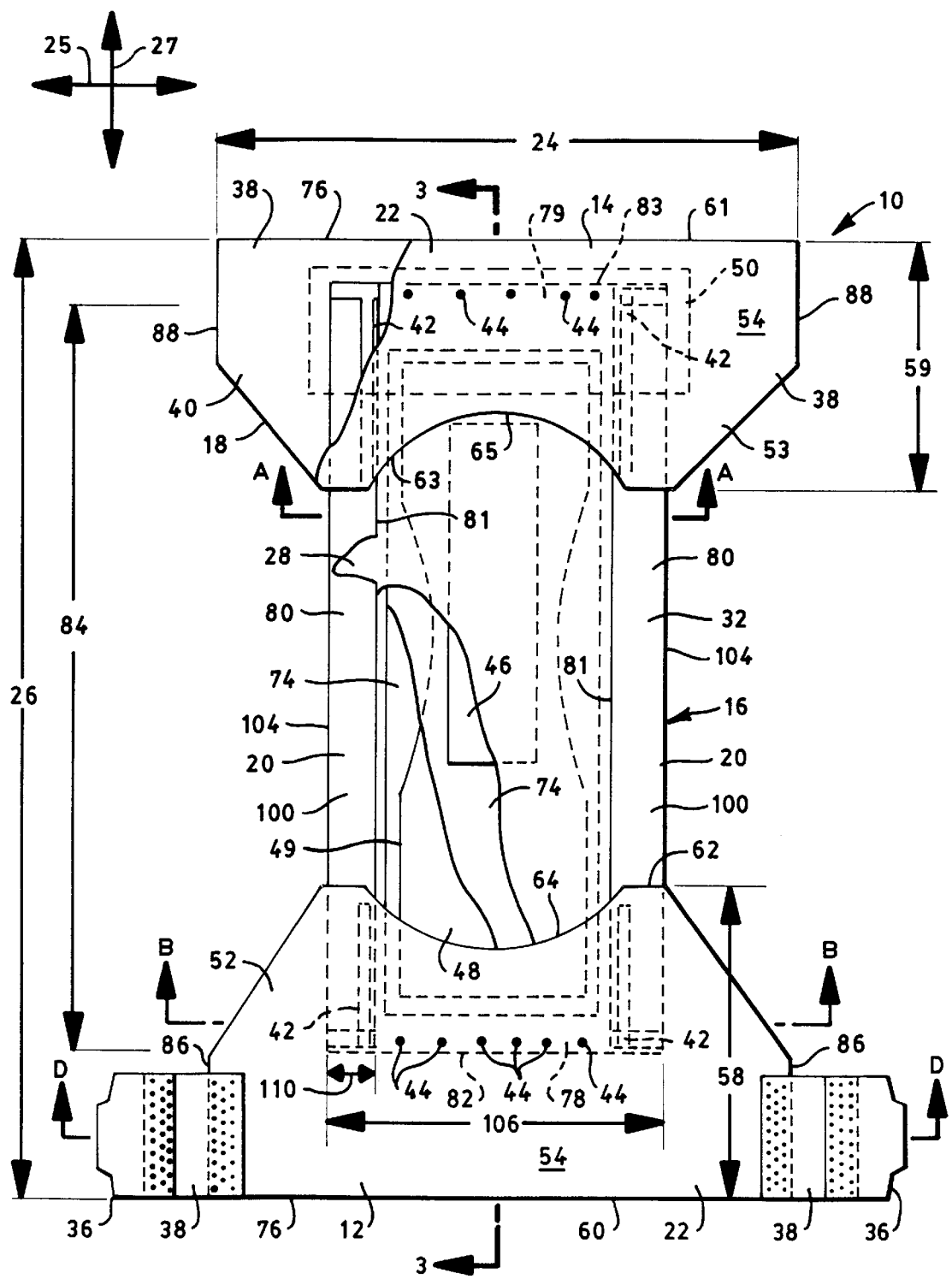
FIG. 1 representatively shows a partially cut-away, inside plan view of the bodyside of an article of the invention.
Figure 2:
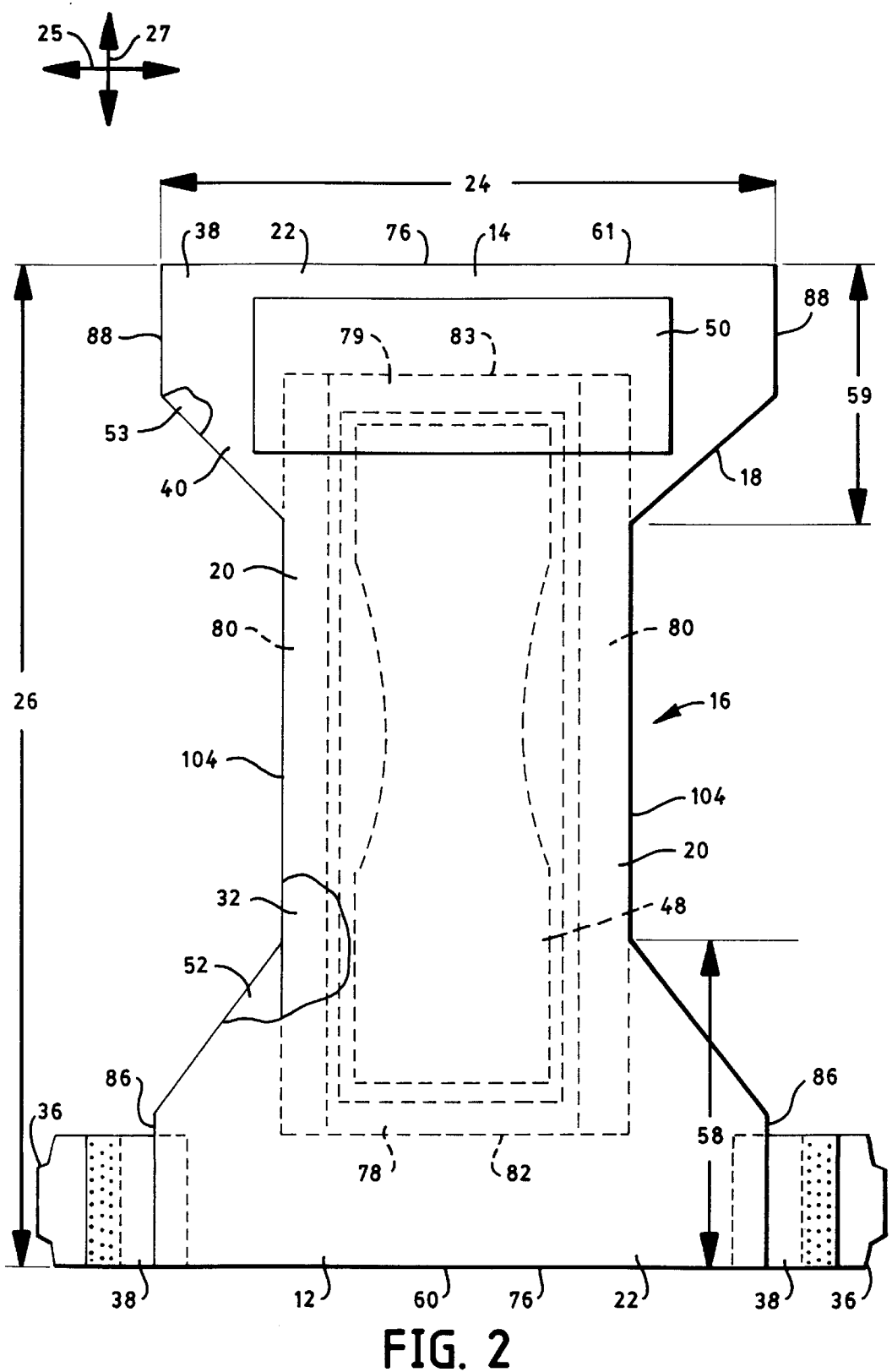
FIG. 2 representatively shows a partially cut-away, outer plan view of the outward side of the article of the invention.
Figure 3:
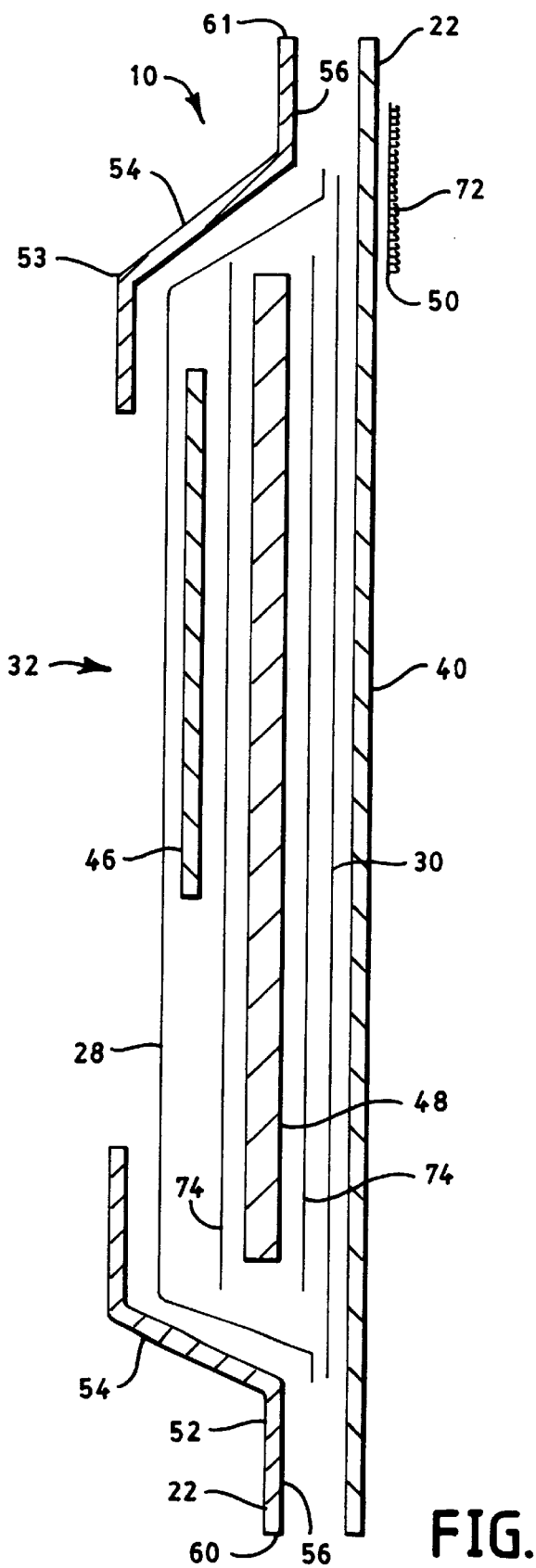
FIG. 3 representatively shows a schematic, longitudinal cross-sectional view with respect to line 3—3 of FIG. 1.

With reference to FIGS. 1 through 3, an article, such as the illustrated integral absorbent article provided by the representatively shown diaper 10, has a longitudinal article length 26 and a lateral article width 24. The article includes an absorbent composite 32 having first and second longitudinally opposed end regions 78 and 79, and at least a first longitudinally terminal end edge 82. The absorbent composite 32 includes a substantially liquid-impermeable backsheet layer 30, a substantially liquid permeable topsheet layer 28, and a retention portion 48 sandwiched between the backsheet and topsheet layers. The retention portion 48 has laterally opposed, terminal side edges 49, and the absorbent composite 32 includes a pair of laterally opposed side margins 80 which extend laterally beyond the side edges 49 of the retention portion 48. A first body panel 52 is joined to the first longitudinal end 78 of the absorbent composite 32. The first body panel 52 has a body side surface 54, an outward surface 56, an outboard terminal end edge 60, and a relatively inboard terminal end edge 62. In desired aspects, the first body panel can have a panel length 58 which is less than the article length 26. In particular aspects of the invention, each of the side margins 80 of the absorbent composite 32 can be inwardly turned toward a longitudinally extending, centerline of the article to provide a turned bodyside surface 100 and a turned outward side surface 102 of each side margin 80. In additional aspects, at least a first portion of the turned bodyside surface 100 of each side margin 80 of the absorbent composite 32 can be secured to the outward surface 56 of the first body panel 52. Such securement can, for example, include at least one body panel attachment 42. Desirably, the securement can include a predetermined system of body panel attachments.

In further aspects of the invention, each of the side margins 80 of the absorbent composite 32 can be inwardly folded, or otherwise inwardly turned in a substantially C-shape (C-turned) to provide a turned section 92 having the turned bodyside surface 100 and the turned outward side surface 102 of each side margin 80. Additionally, each body panel attachment 42 may be located proximate a longitudinally extending, terminal side edge 81 of its corresponding side margin 80. Such placement can help facilitate and accommodate the expansion of the absorbent composite as it absorbs liquid. As representatively shown, each turned section 92 can provide a corresponding, expandable attachment section along at least a portion of each associated side region 80 of the absorbent composite 32 in the first end region 78 of the absorbent composite. Each expandable attachment section can be expandable at least outwardly or at least along the lateral cross-direction of the article width 24, and each expandable attachment section can be configured to secure its correspondingly joined side edge region of the absorbent composite to the outward surface 56 of the first body panel 52.

Figure 1A:
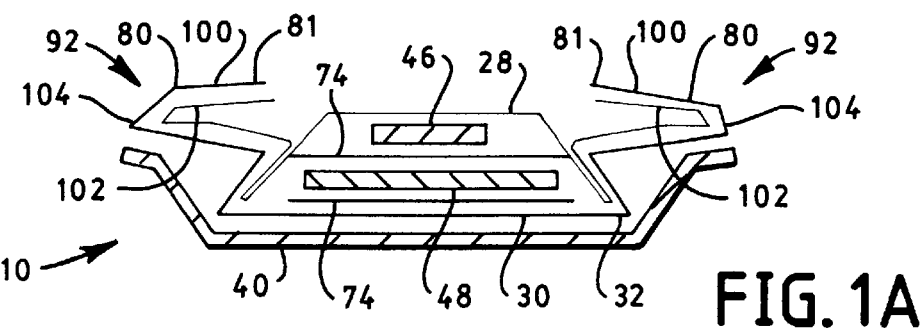
FIG. 1A representatively shows an expanded schematic, lateral cross-sectional view taken with respect to line A—A of FIG. 1.
Figure 1B:
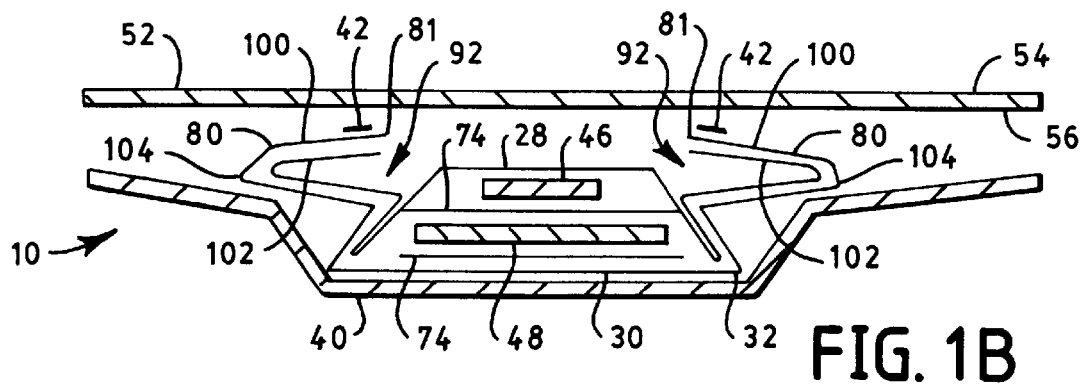
FIG. 1B representatively shows an expanded schematic, lateral cross-sectional view taken with respect to line B—B of FIG. 1 in which a lateral extent of the topsheet layer approximately equals a lateral extent of the backsheet layer.
Figure 1C:
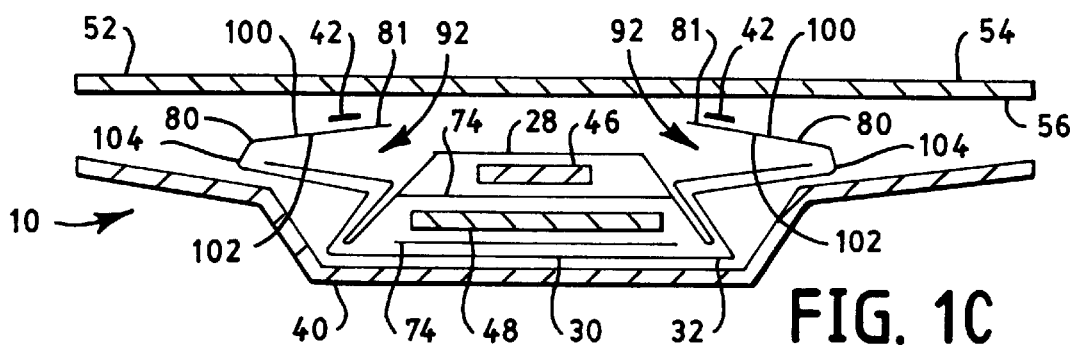
FIG. 1C representatively shows an alternative, expanded schematic, lateral cross-sectional view of FIG. 1B in which the lateral extent of the topsheet layer is less than the lateral extent of the backsheet layer.

With reference to FIGS. 1A through 1C, at least one of the topsheet and backsheet layers 28 and 30, respectively, can extend laterally beyond the side edges 49 of the retention portion 48 to provide the laterally opposed side margins 80 of the absorbent composite 32. In an alternative configuration, each side margin 80 may be a separately provided member 68 which is operatively assembled to the absorbent composite to provide the desired side margins 80, as representatively shown in FIG. 9.

The first body panel 52 is desirably a separately provided member which is attached to and extends across the inwardly facing, bodyside surface of the first end region 78 of the absorbent composite. The first body panel can be joined to the absorbent composite and arranged to provide the back waistband portion 12 of the article. Alternatively, the first body panel 52 may be joined to the absorbent composite and arranged to provide the front waistband portion 14 of the article. In desired configurations, the first body panel 52 can have a longitudinally outboard terminal end edge 60 which is substantially coterminous with a first, longitudinally terminal, end edge of the article. The absorbent composite 32 is attached to extend across and span over an outward surface 56 of the first body panel 52. As representatively shown in FIG. 1, the first body panel 52 can be joined to provide the back waistband portion 12 of the article, and a second body panel 53 can be joined to a longitudinally opposed end of the absorbent composite 32 to provide the front waistband portion 14 of the article.

The second body panel 53 can also be a separately provided member, which is attached to extend across the bodyside surface of the second end region 79 of the absorbent composite. The second body panel 53 has a longitudinal panel length 59 which is less than the article length 26, and the second body panel is longitudinally spaced away from the first body panel 52. In desired configurations, the second body panel 53 can have a longitudinally outboard terminal end edge 61 which is substantially coterminous with a second, longitudinally terminal, end edge of the article. The absorbent composite 32 is attached to extend across and span over an outward surface 56 of the second body panel 53, and as representatively shown, the absorbent composite can operatively extend to interconnect and span between the first and second body panels.

As representatively shown (e.g. FIGS. 1 through 1B), a corresponding, expandable attachment section, such as provided by the turned section 92, can be provided along at least a portion of each associated side region 80 of the absorbent composite 32 in the second end region 79 of the absorbent composite. Each expandable attachment section can be expandable at least outwardly or at least along the lateral cross-direction of the article width 24, and each expandable attachment section can be configured to secure its correspondingly joined side edge region of the absorbent composite to the outward surface 56 of the second body panel 53.

In desired arrangements, the article can have a first waistband portion 12 positioned at the back or rear of the diaper, and a second or front waistband portion 14 positioned longitudinally opposite of the first waistband portion 12. An intermediate, crotch portion 16 interconnects the first and second waistband portion 12 and 14, respectively. In the shown configurations, the intermediate portion is operatively provided by the absorbent composite 32. Leg openings, which are provided at the laterally opposed side margins of the of the intermediate portion of the article, may be elasticized with leg elastics (e.g. FIGS. 4 through 7). A fastening system, such as a system including fasteners 36, is configured to provide a back-to-front fastening in which the back waistband portion 12 can be arranged in an overlapping relation with the front waistband portion 14 to thereby encircle the wearer's body and hold the diaper secure on the wearer during use. Optionally, the fastening system can employ fastener tabs 36 which are configured to provide a front-to-back fastening which arranges and joins the front waistband portion 14 in an overlapping relation with the back waistband portions 12 to thereby encircle the wearer's body during use.

The various aspects of the present invention (individually and in combination) can advantageously help to provide an article having improved fit, improved absorbency and improved resistance to leakage. The article can also be produced at lower cost and with greater efficiency. In particular, the expandable attachment of the absorbent composite to the body panel can allow the absorbent composite to increase in volume during use while maintaining a close and consistent fit of the body panel around the waist and torso of the wearer's body. In addition, the body panel can better provide a more effective barrier between the wet absorbent composite and the wearer's skin. Where leg elastics and appointed portions of the expandable attachment sections are provided at the lateral side margins of the absorbent composite in the intermediate, crotch portion of the diaper, those elasticized and expandable side margins can allow the absorbent composite to grow in volume outwardly, away from the wearer, substantially without affecting the positioning and close fit of the leg elastics about the wearer's legs. As a result, the article of the invention can advantageously provide improved absorbency with reduced leakage.

As representatively shown, the front waistband section 14 of the diaper 10 has a laterally opposed, front pair of side edge regions 88, and the rear waistband section 12 has a laterally opposed, rear pair of side edge regions 86. The intermediate section 16 interconnects the front and rear waistband section and provides a diaper crotch region which is typically positioned between the legs of the wearer. The article may have an appointed fastener landing zone 50 which is disposed on the outward surface of the article. The landing zone may be integrally formed with a component, such as the backsheet layer 30 or the second body panel 53. As representatively shown in FIG. 2, the landing zone 50 may alternatively be a separately provided member which is, for example, disposed on the outward surface of the backsheet layer 30. The liquid permeable topsheet layer 28 is superposed in facing relation with the backsheet layer 30, and the appointed retention portion 48 of the absorbent structure is operably connected and affixed between the backsheet layer 30 and topsheet layer 28. In particular arrangements, the topsheet layer 28 and the retention portion 48 can be constructed to be substantially nonelastomeric and can be operatively attached to the backsheet member 30 to substantially restrain excessive stretching of the backsheet member.

FIGS. 1 and 2 show typical plan views of the representative disposable diaper 10 in its generally flat-out, uncontracted state (i.e., with substantially all elastic induced gathering and contraction removed), and FIG. 1 shows the bodyside surface of the diaper, which is intended to contact the wearer, facing the viewer. The outer edges of the diaper define a periphery with laterally opposed, longitudinally extending side edge margins or regions 20; and longitudinally opposed, laterally extending end edge margins or regions 22. The side edges define leg openings for the diaper, and optionally, are curvilinear and contoured. The end edges are shown as straight, but optionally, may be curvilinear.

With regard to the designated surfaces of the article and components, the various inward surfaces are configured to face toward the body of the wearer when the article is placed about the wearer. The various outward surfaces are configured to face away from the wearer's body when the article is placed about the wearer.

The diaper 10 typically includes a porous, substantially liquid permeable topsheet 28; a substantially liquid impermeable backsheet 30; a retention portion 48 positioned and connected between the topsheet and backsheet; a surge management portion 46 located operatively adjacent to the retention portion; and a system of elastomeric gathering members, such as a system including leg elastics 34 and waist elastics. The surge management portion 46 is positioned in a liquid communication with at least one major facing surface of the retention portion 48, and the topsheet 28, backsheet 30, retention portion 48, surge management portion 46, leg elastics 34, and any waist elastics or other elastomeric members may be assembled together into a variety of well-known diaper configurations. The diaper can additionally include a system of containment flaps (not shown), and a system of side panel or ear region members 38, which may be elasticized or otherwise rendered elastomeric.

Examples of articles which include elasticized side panels and selectively configured fastener tabs are described in U.S. patent application Ser. No. 168,615 of T. Roessler et al., entitled DYNAMIC FITTING DIAPER, and filed Dec. 16, 1993 (attorney docket No. 10,961). Various techniques for forming the desired fastening systems are described in U.S. Pat. No. 5,399,219 of T. Roessler et al., entitled METHOD FOR MAKING A FASTENING SYSTEM FOR A DYNAMIC FITTING DIAPER and issued Mar. 21, 1995

(attorney docket No. 11,186); in U.S. patent application Ser. No. 286,086 of D. Fries, entitled A PROCESS FOR ASSEMBLING ELASTICIZED EAR PORTIONS and filed Aug. 3, 1994 (attorney docket No. 11,169) which issued as U.S. Pat. No. 5,540,796; and in U.S. patent application Ser. No. 08/415,383 of D. Fries, entitled AN ASSEMBLY PROCESS FOR A LAMINATED TAPE and filed Apr. 3, 1995 (attorney docket No. 11,950) which issued as U.S. Pat. No. 5,595,618. The disclosures of the above-described documents are incorporated herein by reference in a manner that is consistent (not in conflict) herewith.

Diaper 10 generally defines the longitudinally extending length dimension 26 and the laterally extending width dimension 24, as representatively shown in FIG. 1. The diaper may have any desired shape, such as rectangular, I-shaped, a generally hourglass shape, or a T-shape. With the T-shape, the crossbar of the "T" may comprise the front waistband portion of the diaper, or may alternatively comprise the rear waistband portion of the diaper.

The topsheet 28 and backsheet 30 may be generally coextensive, and optionally, may be non-coextensive. Either or both of the topsheet 28 and backsheet 30 may have length and width dimensions which are generally larger than and extend beyond the corresponding dimensions of the retention portion 48 to provide end edge margins or regions 78 and 79, and side edge margins or regions 80 of the absorbent composite 32. In particular aspects, the side edge margins of the absorbent composite can be configured to provide at least a portion of the side regions 20 of the article. As representatively shown in FIGS. 1 and 1A, for example, the side margins of the absorbent composite 32 can provide the article side margins along the intermediate portion 16 of the article. The topsheet 28 is operatively associated with and superimposed on backsheet 30, thereby defining the periphery of the diaper. The waistband regions comprise those portions of the diaper, which when worn, wholly or partially cover or encircle the waist or mid-lower torso of the wearer. In the representatively shown configurations, the first and second body panels 52 and 53 are arranged to provide the back and front waistband regions 12 and 14, respectively. The intermediate, crotch region 16 of the article lies between and interconnects the waistband regions 14 and 12, and comprises that portion of the diaper which, when worn, is positioned between the legs of the wearer and covers the lower torso of the wearer. Thus, the intermediate crotch region 16 is an area where repeated liquid surges typically occur in the diaper or other disposable absorbent article.

The backsheet 30 can typically be located along an outer-side surface of the absorbent composite 32 and may be composed of a liquid permeable material, but desirably comprises a material which is configured to be substantially impermeable to liquids. For example, a typical backsheet can be manufactured from a thin plastic film, or other flexible, substantially liquid-impermeable material. As used in the present specification, the term "flexible" refers to materials which are compliant and which will readily conform to the general shape and contours of the wearer's body. The backsheet 30 prevents the exudates contained in the absorbent composite 32 from wetting articles, such as bedsheets and overgarments, which contact diaper 10. In particular embodiments of the invention, the backsheet 30 can include a film, such as a polyethylene film, having a thickness of from about 0.012 millimeters (0.5 mil) to about 0.051 millimeters (2.0 mils). For example, the backsheet film can have a thickness of about 1.25 mil.

Alternative constructions of the backsheet may comprise a woven or nonwoven fibrous web layer which has been totally or partially constructed or treated to impart the desired levels of liquid impermeability to selected regions that are adjacent or proximate the absorbent composite. For example, the backsheet may include a gas-permeable, nonwoven fabric layer laminated to a polymer film layer which may or may not be gas-permeable. Other examples of fibrous, cloth-like backsheet materials can comprise a stretch thinned or stretch thermal laminate material composed of a 0.6 mil (0.015 mm) thick polypropylene cast film and a 0.7 ounce per square yard (23.8 gsm) polypropylene spunbond material (2 denier fibers). A material of this type has been employed to form the outercover of a HUGGIES ULTRATRIM diaper, which has been commercially available from Kimberly-Clark Corporation. The backsheet 30 typically provides the outer cover of the article, and the nonwoven fabric layer typically provides the outward surface of the article. Optionally, however, the article may include a separate outer cover component member which is additional to the backsheet.

Backsheet 30 may include a micro-porous, "breathable" material which permits gases, such as water vapor, to escape from the absorbent composite 32 while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In the various configurations of the invention, where a component, such as the backsheet 30 or the containment flaps are configured to be permeable to gas while having a resistance and limited permeability to aqueous liquid, the liquid resistant component can have a construction which is capable of supporting a selected hydrohead of water substantially without leakage therethrough. A suitable technique for determining the resistance of a material to liquid penetration is Federal Test Method Standard FTMS 191 Method 5514, 1978, or an equivalent thereof.

The backsheet member 30 is sufficiently impermeable liquid and semi-liquid materials to substantially prevent the undesired leakage of waste materials, such as urine and feces. For example, the backsheet member can desirably support a hydrohead of at least about 45 centimeters (cm) substantially without leakage. The backsheet member 30 can alternatively support a hydrohead of at least about 55 cm, and optionally, can support a hydrohead of at least about 60 cm, or more, to provide improved benefits.

The size of the backsheet 30 is typically determined by the size of absorbent composite 32 and the particular diaper design selected. Backsheet 30, for example, may have a generally T-shape, a generally I-shape or a modified hourglass shape, and may extend beyond the terminal edges of the retention portion 48 by a selected distance, such as a distance within the range of about 1.3 centimeters to 2.5 centimeters (about 0.5 to 1.0 inch), to provide at least a portion of the side and end margins.

The topsheet 28 presents a body-facing surface which is compliant, soft-feeling, and non-irritating to the wearer's skin. Further, the topsheet 28 can be less hydrophilic than absorbent composite 32, and is sufficiently porous to be liquid permeable, permitting liquid to readily penetrate through its thickness to reach the absorbent composite. A suitable topsheet layer 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet layer 28 is typically employed to help isolate the wearer's skin from liquids held in the absorbent composite 32.

Various woven and nonwoven fabrics can be used for topsheet 28. For example, the topsheet may be composed of a meltblown or spunbonded web of the desired fibers, and may also be a bonded-carded-web. The various fabrics can be composed of natural fibers, synthetic fibers or combinations thereof.

For the purposes of the present description, the term "nonwoven web" means a web of fibrous material which is formed without the aid of a textile weaving or knitting process. The term "fabrics" is used to refer to all of the woven, knitted and nonwoven fibrous webs.

The topsheet fabrics may be composed of a substantially hydrophobic material, and the hydrophobic material may optionally be treated with a surfactant or otherwise processed to impart a desired level of wettability and hydrophilicity. In a particular embodiment of the invention, topsheet 28 is a nonwoven, spunbond polypropylene fabric composed of about 2.8–3.2 denier fibers formed into a web having a basis weight of about 22 gsm and density of about 0.06 gm/cc. The fabric can be surface treated with an operative amount of surfactant, such as about 0.28% Triton X-102 surfactant. The surfactant can be applied by any conventional means, such as spraying, printing, brush coating or the like.

The topsheet 28 and backsheet 30 are connected or otherwise associated together in an operable manner. As used herein, the term "associated" encompasses configurations in which topsheet 28 is directly joined to backsheet 30 by affixing topsheet 28 directly to backsheet 30, and configurations wherein topsheet 28 is indirectly joined to backsheet 30 by affixing topsheet 28 to intermediate members which in turn are affixed to backsheet 30. Topsheet 28 and backsheet 30 can, for example, be joined to each other in at least a portion of the diaper periphery by attachment mechanisms (not shown) such as adhesive bonds, sonic bonds, thermal bonds, pinning, stitching or any other attachment techniques known in the art, as well as combinations thereof. For example, a uniform continuous layer of adhesive, a patterned layer of adhesive, a sprayed pattern of adhesive or an array of separate lines, swirls or spots of construction bonds may be used to affix the topsheet 28 to the backsheet 30. It should be readily appreciated that the above-described attachment mechanisms may also be employed to suitably interconnect, assemble and/or affix together the various other component parts of the articles which are described herein.

The absorbent body or composite 32 provides an absorbent structure which includes a retention portion 48 for holding and storing absorbed liquids and other waste materials, such as the shown absorbent pad composed of selected hydrophilic fibers and high-absorbency particles. The absorbent composite is positioned and sandwiched between the topsheet 28 and backsheet 30 to form the diaper 10. The absorbent composite has a construction which is generally compressible, conformable, non-irritating to the wearer's skin, and capable of absorbing and retaining body exudates. It should be understood that, for purposes of this invention, the absorbent composite structure may comprise a single, integral piece of material, or alternatively, may comprise a plurality of individual separate pieces of material which are operably assembled together.

Various types of wettable, hydrophilic fibrous material can be used to form the component parts of absorbent composite 32 particularly the retention portion 48. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with such system, fibers having contact angles less than 90° are designated "wettable", while fibers having contact angles greater than 90° are designated "nonwettable".

The absorbent composite structure 32 can comprise a retention portion having a matrix of hydrophilic fibers, such as a web of cellulosic fluff, mixed with particles of high-absorbency material. In particular arrangements, the retention portion 48 of the absorbent composite 32 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be non-uniformly mixed. For example, the concentrations of superabsorbent particles may be arranged in a non-step-wise gradient through a substantial portion of the thickness (z-direction) of the absorbent structure, with lower concentrations toward the bodyside of the absorbent composite and relatively higher concentrations toward the outside of the absorbent structure. Suitable z-gradient configurations are described in U.S. Pat. No. 4,699,823 issued Oct. 13, 1987 to Kellenberger et al., the entire disclosure of which is incorporated herein by reference in a manner that is consistent (not in conflict) with the present description. Alternatively, the concentrations of superabsorbent particles may be arranged in a non-step-wise gradient, through a substantial portion of the thickness (z-direction) of the absorbent structure, with higher concentrations toward the bodyside of the absorbent composite and relatively lower concentrations toward the outside of the absorbent structure. The superabsorbent particles may also be arranged in a generally discrete layer within the matrix of hydrophilic fibers. In addition, two or more different types of superabsorbent may be selectively positioned at different locations within or along the fiber matrix.

The high-absorbency material may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent composite include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in absorbent composite 32 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in absorbent composite 32. Desired for use are particles having an average size of from about 20 microns to about 1 millimeter. "Particle size" as used herein means the weighted average of the smallest dimension of the individual particles.

The hydrophilic fibers and high-absorbency particles can be configured to form an average composite basis weight which is within the range of about 400–900 gsm. In certain aspects of the invention, the average composite basis weight is within the range of about 500–800 gsm, and alternatively is within the range of about 550–750 gsm to provide desired performance.

To improve the containment of the high-absorbency material, absorbent composite structure 32 can include an overwrap, such as wrap sheet 74, which is placed immediately adjacent and around the retention portion 48, and may be bonded to the absorbent structure and to the various other components of the article. The wrap sheet is preferably a layer of absorbent material which covers the major bodyside and outerside surfaces of the retention portion, and preferably encloses substantially all of the peripheral edges of the retention portion to form a substantially complete envelope thereabout. Alternatively, the wrap sheet can provide an absorbent wrapping which covers the major bodyside and outerside surfaces of the retention portion, and encloses substantially only the lateral side edges of the retention portion. Accordingly, both the linear and the inwardly curved portions of the lateral side edges of the wrap sheet would be closed about the retention portion. In such an arrangement, however, the end edges of the wrap sheet may not be completely closed around the end edges of the absorbent composite at the waistband regions of the article.

For example, the complete wrap sheet 74, or at least the bodyside layer of the wrap sheet, may comprise a meltblown web composed of meltblown fibers, such as meltblown polypropylene fibers. Another example of the absorbent wrap 74 may comprise a low porosity cellulosic web, such as a tissue composed of an approximately 50/50 blend of hardwood/softwood fibers.

The absorbent wrap 74 may comprise a multi-element wrapsheet which includes a separate bodyside wrap layer and a separate outerside wrap layer, each of which extends past all or some of the peripheral edges of the retention portion 48. Such a configuration of the wrap sheet can, for example, facilitate the formation of a substantially complete sealing and closure around the peripheral edges of the retention portion 48. In the back waistband portion of the illustrated diaper, the absorbent wrap may also be configured to extend an increased distance away from the periphery of the retention portion to add opacity and strength to the back side-sections of the diaper. In the illustrated embodiment, the bodyside and outerside layers of absorbent wrap 74 can extend at least about ½ inch beyond the peripheral edges of the retention portion to provide an outwardly protruding, flange-type bonding area over which the periphery of the bodyside portion of the absorbent wrap may be completely or partially connected to the periphery of the outerside portion of the absorbent wrap.

The bodyside and outerside layers of wrap sheet 74 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs.

The diaper 10 can also include a surge management layer 46 which helps to decelerate and diffuse surges of liquid that may be introduced into the absorbent composite of the article. The surge layer 46 can also temporarily hold the liquid for a limited period of time, spread and direct the distribution of the liquid, and then release the liquid for absorption into the retention portion 48. In the illustrated embodiment, for example, the surge layer 46 can be located on an inwardly facing body side surface of the topsheet layer 28. Alternatively, the surge layer 46 may be located adjacent to an outer side surface of the topsheet 28 to be interposed between the topsheet 28 and the retention portion 48.

Examples of suitable surge management layers 46 are described in U.S. patent application Ser. No. 206,986 of C. Ellis and D. Bishop, entitled FIBROUS NONWOVEN WEB SURGE LAYER FOR PERSONAL CARE ABSORBENT ARTICLES AND THE LIKE, filed Mar. 4, 1994 (attorney docket No. 11,256) which corresponds to U.S. Pat. No. 5,486,166; and U.S. patent application Ser. No. 206,069 of C. Ellis and R. Everett, entitled IMPROVED SURGE MANAGEMENT FIBROUS NONWOVEN WEB FOR PERSONAL CARE ABSORBENT ARTICLES AND THE LIKE, filed Mar. 4, 1994 (attorney docket No. 11,387) which corresponds to U.S. Pat. No. 5,490,846; the entire disclosures of which are hereby incorporated by reference in a manner that is consistent herewith.

Each body panel 52 and 53 can have a desired shape, which may be generally rectangular, or non-rectangular. As representatively shown, each body panel can extend longitudinally past its corresponding end edge of the topsheet layer 28 and/or can extend laterally beyond its corresponding end edge of the backsheet layer 30. Optionally, either or both body panels can have longitudinally outboard edges which are substantially coterminous with their corresponding end edges of the topsheet layer 28 and/or backsheet layer 30. Laterally opposed, side-end sections of the body panel can extend transversely beyond the side edges of the absorbent composite 32 to provide extending ear portions 38 of the article. Accordingly, each body panel can extend across substantially the entire cross-directional width of its corresponding waistband portion of the article. Each body panel can extend laterally beyond the side edges of the topsheet layer 28 and/or can extend laterally beyond the side edges of the backsheet layer 30. In particular arrangements, the body panel can be configured with lateral end sections which have a tapered shape to provide tapered ear portions. Each tapered ear portions can have a relatively longer longitudinal length adjacent the side margins of the absorbent composite, and a relatively shorter longitudinal length at the laterally distal ends of the ear portion.

In desired arrangements, at least a medial portion 64 of the laterally extending and longitudinally inboard edge 62 of the first body panel 52 can be substantially unattached to bodyside surface of the absorbent composite 32. Similarly, the second body panel 53 can have a longitudinally inboard terminal end edge 63, and at least a medial portion 65 of the end edge 63 can be substantially unattached to the absorbent composite 32. Either or both of the inboard edges may be substantially straight or curved, as desired. In particular aspects, at least a portion of the inboard edge of either or both of the body panels 52 and 53 can be arranged in a configuration which is concave-inboard, as illustrated in FIG. 1. As representatively shown, the appointed concave curvature can commence at each side margin of the absorbent composite, and can traverse generally laterally across the absorbent composite with a middle portion of the curvature displaced toward the longitudinal end of the article. The curvature can help provide an improved conformance of the body panel with the contours of the wearer's body.

In other aspects of the invention, the first longitudinally terminal end edge 82 of substantially the entire absorbent composite 32 can be spaced relatively inboard from the longitudinally outboard, terminal end edge 60 of the first body panel 52. Accordingly, the body panel can extend longitudinally past and project length-wise beyond its corresponding, generally adjacent, terminal end edge 82 of the absorbent composite. Similarly, the second longitudinally terminal end edge 83 of substantially the entire absorbent composite 32 can be spaced relatively inboard from the longitudinally outboard, terminal end edge 61 of the second body panel 53. Accordingly, the second body panel can extend longitudinally past and project length-wise beyond its corresponding, generally adjacent, terminal end edge 82 of the absorbent composite.

During the conditions of ordinary use, the expandable attachment sections provided by the turned sections 92 can advantageously allow and provide for a controlled expansion of the volume of the absorbent composite 32, especially after the absorbent composite has started absorbing liquids. In the various configurations of the invention, each expandable attachment section may be a separately provided member which is assembled into the article, or may be integrally formed from appointed portions of other existing components of the article. For example, the expandable attachment section may be formed from appointed portions of the backsheet 30, topsheet 28 or operative combinations thereof. In particular aspects of the invention, the various expandable attachment sections can be substantially free of absorbent materials, such as hydrophilic fiber and superabsorbent polymers. Optionally, the various expandable attachment sections can include a selected quantity of absorbent materials.

With reference to FIGS. 1 through 1C, for example, the expandable attachment section of the article can include at least one C-folded, or otherwise C-turned member or portion 92, and the C-turned portion can be provided at each side margin region 80 of the absorbent composite 32 to provide the turned bodyside surface 100 and the turned outward side surface 102 of each side margin 80. In the representatively shown arrangements, for example, the C-turned portion can provide a predetermined arrangement of layers or panels which can be flattened together to provide an initial low-volume configuration for the absorbent composite 32. During use and especially during the absorption of liquid, the layers can operatively be moved apart in an outward direction and/or lateral direction to provide a substantially continuous series of one or more, incrementally higher-volume configurations for cooperation with an increasing volume of the absorbent composite, particularly the increasing volume of the retention portion 48.

Figure 9:
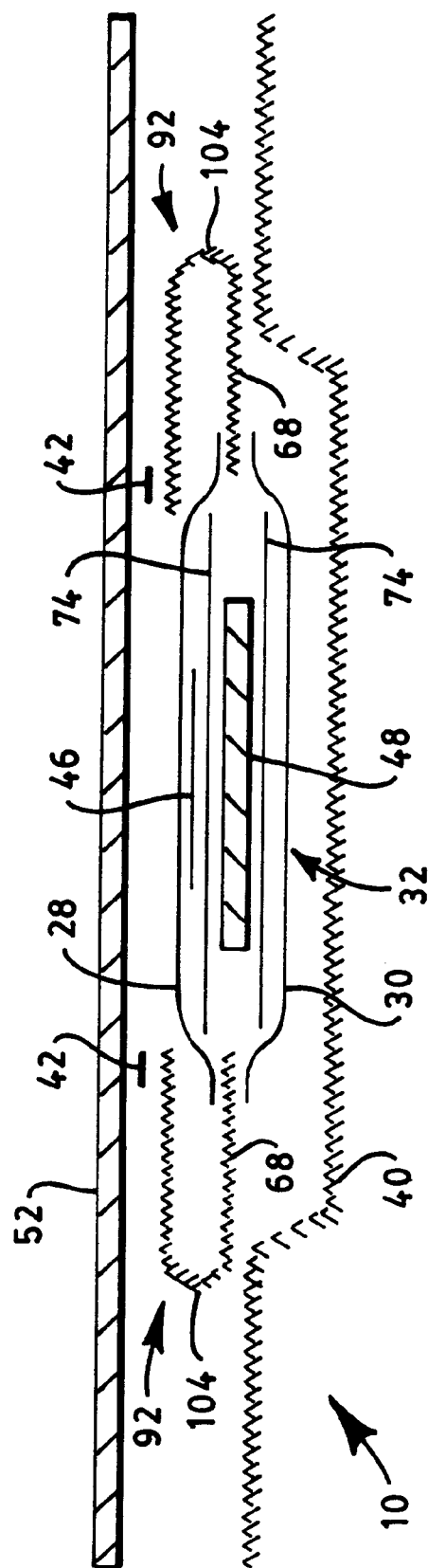
FIG. 9 representatively shows a lateral cross-sectional view of an article having turned side margins formed by a separately provided member.

In particular aspects, the extendible attachment section can include a separately provided, C-turned component 68 which is assembled and joined to interconnect between the absorbent composite 32 and the outward surface 56 of the first body panel 52, as representatively shown in FIG. 9. Alteratively, the substantially C-turned portion 92 can be provided by appointed side marginal sections of the topsheet layer 28 and/or the backsheet layer 30 which extend laterally beyond the terminal side edges of the retention portion 48. As representatively shown in FIGS. 1A and 1B, the C-turned portion may include side marginal sections of both the topsheet layer 28 and the backsheet layer 30. In this example, the side margins of both the substantially liquid-impermeable backsheet 30 and the substantially liquid permeable topsheet 28 can extend laterally past and project beyond the terminal side edges of the retention portion 48 and wrapsheet 74. The combined side margins of the projecting backsheet and topsheet layers can then be C-turned to form the desired expandable attachment section.

As representatively shown in FIG. 1C, the C-turned portion may alternatively include side marginal sections of only the backsheet layer 30. In this example, the side margins of the substantially liquid-impermeable backsheet 30 can extend laterally past and beyond the terminal side edges of the retention portion 48 and wrapsheet 74. The extended side margins of the backsheet layer 30 can then be C-turned along a laterally inward direction to form the desired expandable attachment section. Optionally, either or both of the backsheet layer 30 and topsheet layer 28 may be configured to be laterally extensible. For example, either or both of the backsheet layer 30 and topsheet layer 28 may be configured to be substantially elastomeric. In particular arrangements, at least a marginal side region of either or both of the backsheet layer 30 and topsheet layer 28 may be configured to be laterally extensible.

The relatively outboard edge of each C-turned portion 92 can be operatively attached to its associated body panel 52 or 53 at a location which is positioned laterally inboard from its corresponding, longitudinally extending, terminal side edge of the associated body panel. Accordingly, the expandable attachment section provided by the turned portion 92 can provide a mechanism for allowing the absorbent composite 32 to expand outwardly and away from the body panels and from the wearer's body.

With regard to the substantially C-turned members 92, the C-turned members can extend longitudinally along the article length 26. As representatively shown, the turned members 92 extend substantially continuously along the article length, but may optionally extend in a discontinuous configuration. Desirably, the immediately adjacent, face-to-face panels regions within the C-portion of the turned sections 92 are substantially unattached to each other. Optionally, a small amount of an adhesive or other type of bond may be employed to lightly attach together two or more of the adjacent panels. Such attachment between the panels, however, should be configured with a strength and distribution which do not excessively inhibit the desired expansions and moving apart of the attachment sections. When the retention portion 48 absorbs liquid and increases in volume, the resultant expansion of the retention portion exerts a tensile stress on the expandable attachment sections. The subsequent expansion of the turned sections 92 operatively relieves the applied stresses and increases the volume of the retention portion 48 in a manner which allows the retention portion to grow outwardly away from the body panels 52 and 53. As a result, the first and/or second body panels can maintain its desired fit closely about a wearer's body, and can better resist the formation of gaps or sags that might allow excessive, undesired leakage.

Figure 5:
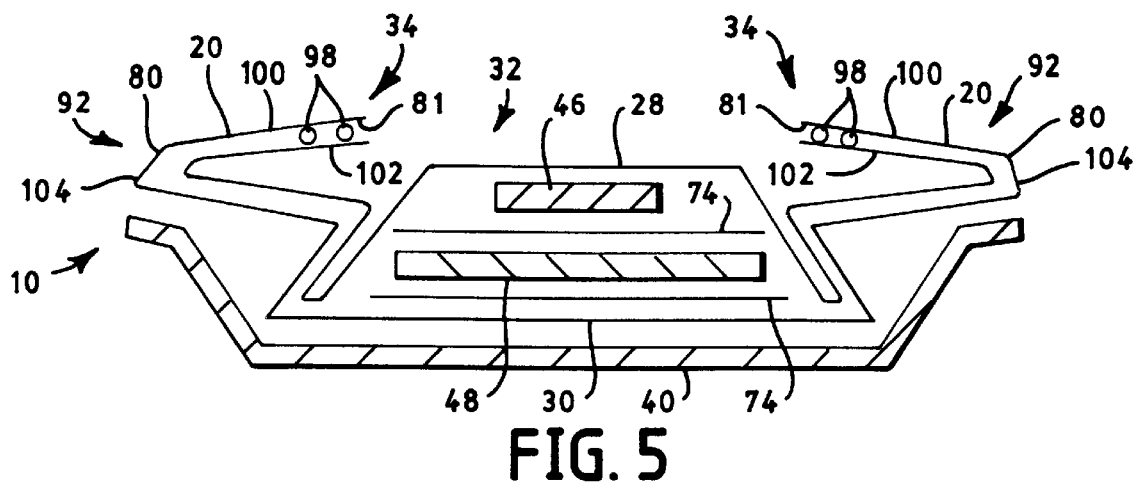
FIG. 5 representatively shows an expanded schematic, lateral cross-sectional view of an article of the invention having elastomeric members joined to the turned-in side margins of the absorbent composite, with respect to line 5—5 of FIG. 4.
Figure 5A:
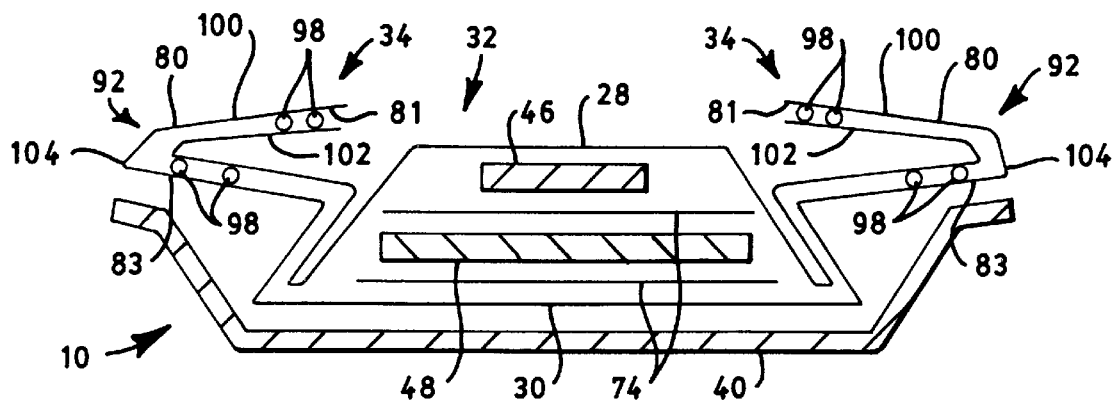
FIG. 5A representatively shows an expanded schematic, lateral cross-sectional view of an article of the invention having another configuration of elastomeric members joined to the turned-in side margins of the absorbent composite.
Figure 5B:
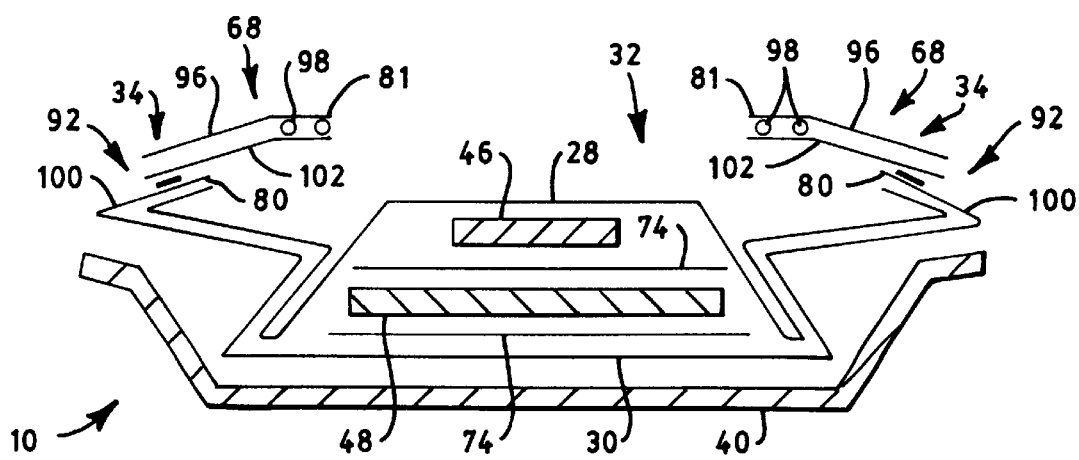
FIG. 5B representatively shows an expanded schematic, lateral cross-sectional view of an article of the invention having a separately provided elastomeric component which is assembled and joined to each of the turned-in side margins of the absorbent composite.

In particular aspects, each of the side margins 80 of the absorbent composite 32 may include a separately provided component 68 which is assembled and attached into the article, as representatively shown in FIGS. 5B and 9. The side margin component 68 may be formed from various suitable materials, such woven or nonwoven creped fabrics, polymer films, creped films, apertured films, knitted fabrics and the like, as well as combinations thereof.

In particular aspects of the invention, each expandable attachment section (e.g. each C-turned portion 92) can provide a transverse elongation (along the lateral direction 25) of at least about 1 cm when subjected to an applied, lateral tensile force of 30 grams-force (gmf) per inch of cross-wise length of the expandable attachment section (about 12 gmf per cm of cross-wise length; about 0.12 Newtons per cm of cross-wise length). Alternatively, the expandable attachment section can provide an elongation of at least about 2 cm, and optionally, an elongation of at least about 4 cm under the applied tensile force to afford improved performance. In other aspects, the expandable attachment section can provide an elongation of not more than about 12 cm under an applied tensile force of 50 gmf per inch of cross-wise length of the expandable attachment section (about 20 gmf per cm of cross-wise length; about 0.19 Newtons per cm of cross-wise length). Alternatively, the expandable attachment section can provide an elongation of not more than about 10 cm, and optionally is not more than about 8 cm to afford improved benefits. For the purposes of this elongation parameter, the cross-wise length of the expandable attachment section is measured perpendicular to the applied tensile force. For a sample taken from the illustrated configurations of the invention, the cross-wise length of the sample would lie generally along the article longitudinal direction 27.

A suitable technique for generating a representative tensile-load vs. extension curve, and for determining the amount of elongation and/or retractive force parameters of a selected component or material can employ ASTM Standard Test Method D882 (Tensile Method for Tensile Properties of Thin Plastic Sheeting) dated December 1995, with the following particulars. The "width" of the test sample will be a cross-wise width which can be conveniently obtained from the product being tested, and is desirably about 2 inch (about 5.04 cm). The test sample width is perpendicular to the direction of the tensile force applied during the testing. With regard to the shown configurations, for example, the test sample width generally corresponds to the length-wise dimension of the expandable attachment section along the longitudinal direction 27 of the article. The initial separation of the jaws of the tensile tester is 3 inches (7.62 cm), and the moving jaw is moved at a constant rate of 50 mm/min. The moving jaw is stopped at an extension of 50 mm for a period of 10 sec, and then returned back to its initial starting position at a rate of 50 mm/min. The force-extension curve to the complete tension and retraction cycle can be recorded on a conventional computer equipped with commercially available software, such as TestWorks for Windows, version 3.09, which is available from MTS System Corporation, a business having a location at 14000 Technology Drive, Eden Prairie, Minn. The obtained data is normalized and reported in appropriate units of force per unit length, such as grams-force per inch or grams-force (or Newtons) per centimeter of sample "width".

With reference to FIGS. 1 and 1B, each expandable turned section 92 can be bonded or otherwise affixed to its correspondingly associated region of the body panel with an operative side securement 42. Each side securement 42 may be substantially continuous or discontinuous, and may be distributed randomly or in a selected area pattern. Additionally, each body panel attachment 42 can be located proximate a longitudinally extending, terminal side edge 81 of its corresponding side margin 80.

The article of the invention can further include a first, laterally extending, end attachment 44 which is distributed along at least a portion of the first end region 78 of the absorbent composite 32 to help secure the end of the absorbent composite to the body panel 52. The end attachment 44 may also be configured to provide a sealing, liquid-barrier attachment which can help resist a passage of liquid between the absorbent composite and the outward surface 56 of the first body panel 52. Similarly, a second laterally extending end attachment 44 can be distributed along at least a portion of the second end region 79 of the absorbent composite 32 to secure the second end of the absorbent composite to the second body panel 53, and to help resist a passage of liquid between the absorbent composite and the outward surface 56 of the second body panel 53.

The side securements 42 and end attachments 44 can be provided by various suitable mechanisms. For example, each of the side securements 42 and end attachments 44 may include adhesive bonds, thermal bonds, ultrasonic bonds, pins, staples, or the like, as well as combinations thereof.

In the representatively shown configuration, each end attachment 44 is provided by a plurality of individually spaced apart, thermal or ultrasonic bonds arranged in a selected pattern. The pattern bond may be regular or irregular in distribution, and is operatively configured to provide the desired securement, expandability and/or leakage resistance in the article. Each end attachment 44 may alternatively include a laterally extending bond which is substantially continuous along a major portion of the lateral width of the absorbent composite. Similarly, each side securement 42 may include a longitudinally extending bond which is substantially continuous along a major portion of the longitudinal length of the article portion at which each expandable attachment section is operably affixed to its corresponding, associated body panel.

In particular aspects of the invention, either or both of the body panels 52 and 53 may be composed of a wide range of materials with various basis weights and properties. For example, the body panel material may include knitted or other woven fabrics, nonwoven fabrics, polymer films, laminates, and the like, as well as combinations thereof. It should be readily appreciated that each of the individual body panels may be composed of different materials, or of substantially the same material.

In the various configurations of the invention, the basis weight of the body panel material can be at least a minimum of about 10 g/m². Alternatively, the basis weight can be at least about 20 g/m², and optionally, can be at least about 40 g/m² to provide improved benefits. In further aspects, the basis weight of the body panel material can be not more than a maximum of about 100 g/m². Alternatively, the basis weight can be not more than about 80 g/m², and optionally, can be not more than about 60 g/m² to provide improved performance.

In the differing configurations of the invention, the body panel material may be substantially permeable to air or substantially impermeable to air. The body panel material also may be substantially liquid-permeable or substantially liquid-impermeable. In particular arrangements, the body panel material may be substantially nonelastomeric. In other aspects, the body panels 52 and/or 53 can include an elastomeric material which is elastomerically stretchable at least along the lateral article width 24. Examples of such elastomeric materials can include a neck-bonded-laminate (NBL), a stretch-bonded-laminate (SBL), a necked-thermal laminate, or the like, as well as combinations thereof. Such laminates can provide an improved combination of cloth-like feel and elastomeric stretchability.

In desired configurations, the elastomeric body panel material can provide an elastomeric, stretch elongation which is at least about 3%, and desirably is at least about 5%. Alternatively, the stretch elongation can be at least about 10%, and optionally, can be at least about 20% to provide improved performance. In other aspects, the elastomeric stretch elongation can be not more than about 200% and desirably can be not more than about 100%. Alternatively, the stretch elongation can be not more than about 50%, and optionally, can be not more than about 30% to provide improved performance.

The percentage of elastomeric stretch or other elongation can be determined in accordance with the following formula: $100*(L-L_o)/(L_o)$;

where: L=elongated length,
$L_o$=initial length,

In addition, the amount of stretch elongation is determined under an applied tension force of 250 gram-force per inch of width measured perpendicular to the direction of the applied tension.

With reference to FIG. 1, the first body panel 52 and/or the second body panel 53 can have a longitudinal length 58, 59 which is not more than a maximum of about 80% of the article length 26. Alteratively, either or both body panels can alternatively have a longitudinal length which is not more than about 65% of the article length 26, and optionally, is not more than about 50% of the article length to provide improved benefits. In desired arrangements, the longitudinal length of the body panel can be not more than about 40%. In further arrangements, the longitudinal length of the body panel can be not more than about 35%, and optionally not more than about 30% of the article length to provide improved performance.

In other aspects of the invention, the first body panel 52 and/or the second body panel 53 can have a longitudinal length which is at least a minimum of about 5% of the article length 26. Alternatively, at least one of the body panels (or both) can have a longitudinal length which is at least about 10% of the article length, and optionally, is at least about 15% of the article length to provide improved performance. Desirably, at least one of the body panels, particularly the back body panel, can have a longitudinal length which is at least about 2 cm. More desirably the selected body panel can have a longitudinal length which is at least about 4 cm, and optionally, is at least about 6 cm to provide improved fit and skin dryness.

With reference to FIG. 1, the side margins 80 of the absorbent composite 32 can be inwardly turned along corresponding turning lines 104 which are substantially parallel to each other. With respect to an alternative configuration representatively shown in FIG. 8, the side margins 80 of the absorbent composite 32 can be inwardly turned along corresponding turn lines 104 which are substantially non-parallel to each other. In the representatively shown configuration, the turning lines 104 are relatively further apart from each other at the first longitudinal end region 78 of the absorbent composite 32, as compared to the distance between the turning lines 104 at the second longitudinal end region 79 of the absorbent composite. In an optional configuration, the turning lines 104 can be positioned relatively closer to each other at the first longitudinal end region 78 of the absorbent composite 32.

The width 106 of the absorbent composite 32 at the second end region 79 of the absorbent composite can be relatively smaller than the width of the absorbent composite at the absorbent composite first end region 78. In addition, a distance 108 between the terminal side edges 81 of the absorbent composite at the absorbent composite second end region 78 can be less than the distance between the side edges 81 of the absorbent composite at the absorbent composite first end region 78. The relatively smaller width 108a of the absorbent composite at the second end region 79 of the absorbent composite can help provide an improved fit within the narrow crotch region of the wearer. The relatively wider width 108 of the absorbent composite at its first end region 78 can help provide a wider fit around the buttocks area of the wearer.

Each side margin 80 of the absorbent composite can have an inwardly turned width dimension 110 (e.g. FIG. 1) which is at least about 0.5 cm. The turned width 110 of each side margin can alternatively be at least a minimum of about 1 cm, and optionally, can be at least about 1.5 cm to provide improved performance. In further aspects of the invention, each side margin 80 of the absorbent composite can have an inwardly turned width dimension 110 which is not more than a maximum of about 7 cm. The turned width 110 of each side margin can alternatively be not more than about 6 cm, and optionally, can be not more than about 5 cm to provide improved benefits.

Figure 8:
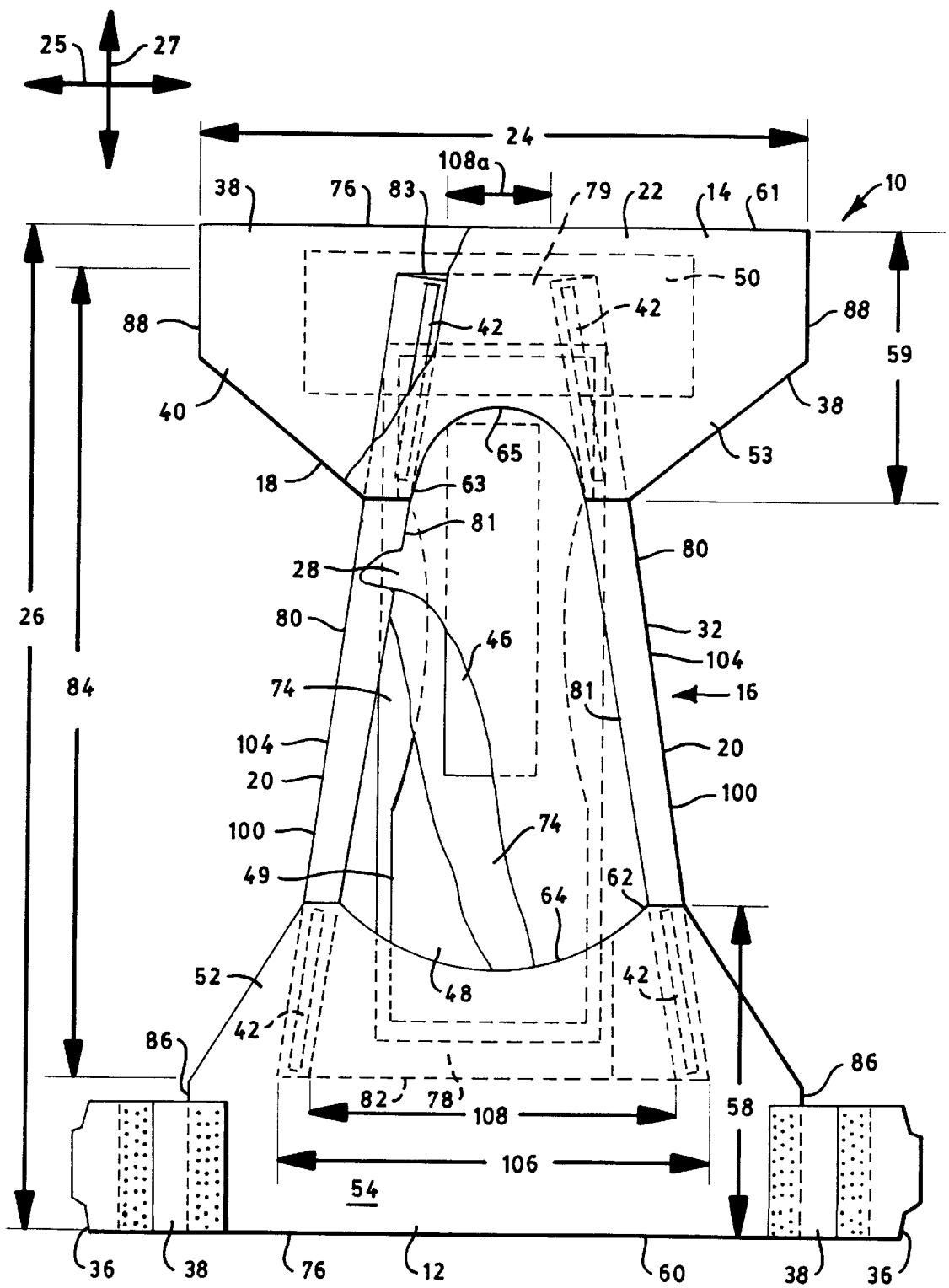
FIG. 8 representatively shows a partially cut-away, plan view of the inside, bodyside surface of still another article of the invention which includes turned side margins that have been turned about non-parallel turning lines.

As representatively shown in FIG. 8, the turned width dimension 110 at one end of the article can be different than the turned width dimension at the opposite end of the article. For example, the turned width dimension 110 at the appointed front waistband end 14 of the article can be larger than the turned width dimension at the appointed back waistband end 12 of the article.

In particular aspects, the distance 108 between the inwardly positioned side edges 81 of the absorbent composite 32 can be at least a minimum of about 0.5 cm. The distance 108 between the inwardly positioned side edges 81 of the absorbent composite can alternatively be at least about 0.75 cm, and optionally, can be at least about 1 cm to provide improved performance. In further aspects of the invention, the distance 108 between the inwardly positioned side edges 81 of the absorbent composite 32 can be not more than a maximum of about 4 cm. The distance 108 between the inwardly positioned side edges 81 of the absorbent composite can alternatively be not more than about 3 cm, and optionally, can be not more than about 2.5 cm to provide improved benefits.

Figure 4:
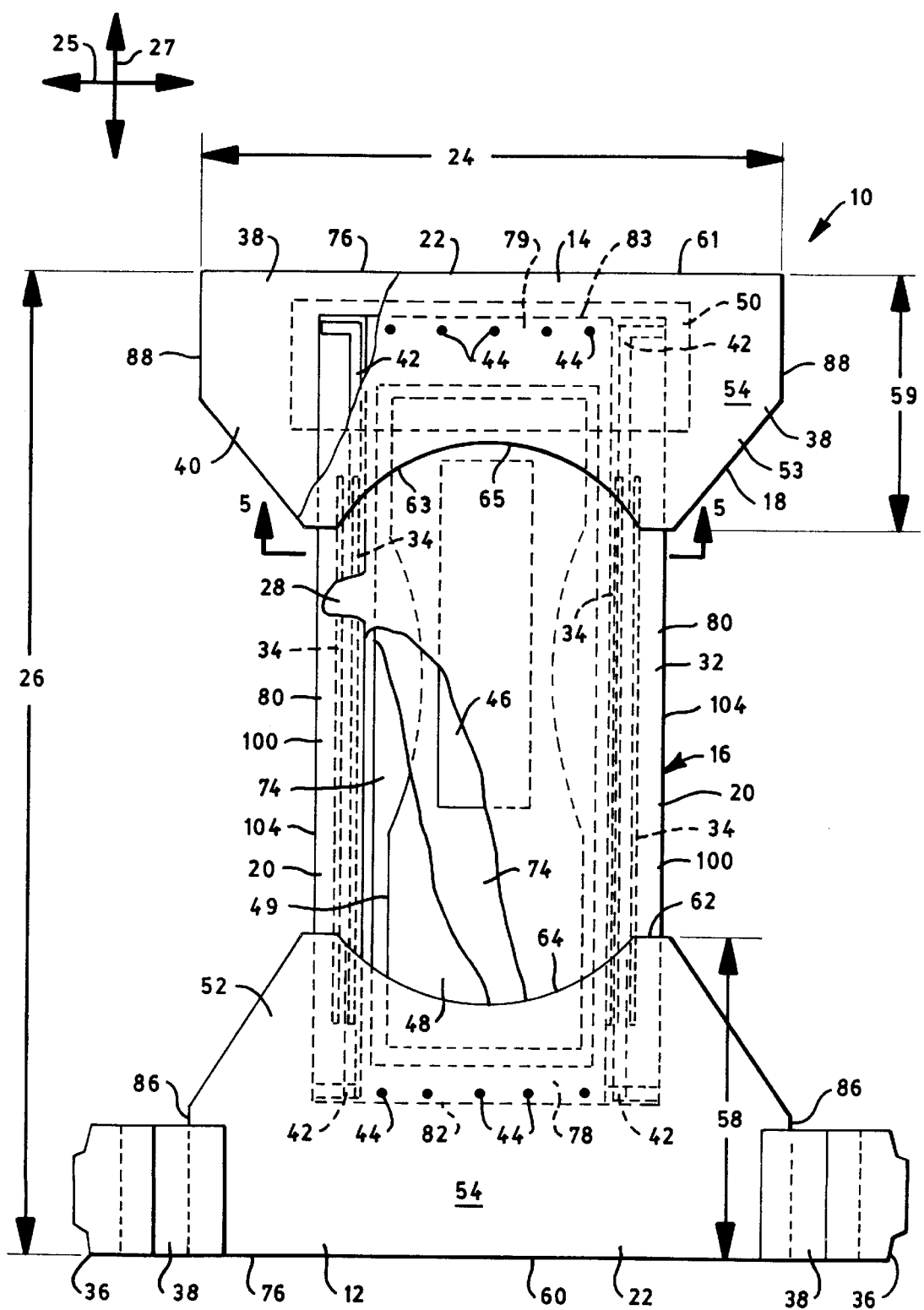
FIG. 4 representatively shows a partially cut-away, plan view of the inner, bodyside surface of an article of the invention which includes leg elastic members.

As representatively shown in FIG. 4, the absorbent article can further include at least one elastomeric member attached to provide an operative, longitudinally extending, leg elastic member 34. Each of the leg elastic members 34 can be operatively attached to an inward or outward surface of at least a portion of the lateral side edge regions 20 of the article. In the shown configuration, for example, the side edge regions 20 of the article are provided by the side margins 80 of the absorbent composite 32 which extend laterally beyond the laterally opposed, terminal side edges 49 of the retention portion 48. It should be readily appreciated that any of the conventional attaching mechanisms described in the present disclosure may be employed to secure the leg elastic members into the article. In the representatively shown arrangement, the attachment mechanism can include a distributed pattern of sonic bonds.

The elastic members 34 may have any of a multitude of configurations. For example, the overall width of the individual elastic members 34 may be varied from about 0.25 millimeters (0.01 inch) to about 25 millimeters (1.0 inch) or more. The elastic members may comprise a single strand of elastic material, or may comprise several parallel or non-parallel strands 98 of elastic material and the elastic members may be applied in a rectilinear or curvilinear arrangement. Where the strands are non-parallel, two or more of the strands may intersect or otherwise interconnect within the elastic member. In particular arrangements, the elastic members may include elastomeric strands 98 which are optionally located and laminated between the topsheet layer 28 and backsheet layer 30 of the absorbent composite 32. The elastic members may be affixed to the diaper in any of several ways which are known in the art. For example, the elastic members may be ultrasonically bonded, heat and pressure sealed using a variety of bonding patterns, or adhesively bonded to the diaper 10 with sprayed or swirled patterns of hotmelt adhesive.

In particular aspects, the at least one elastomeric member can be attached proximate to a terminal side edge region 81 of each side margin 80 of the absorbent composite 32, as representatively shown in FIGS. 4 through 5B. In another aspect of the invention, the at least one elastomeric member can be attached to a laterally outboard region 83 of each side margin 80 of the absorbent composite, as representatively shown in FIG. 5A. In desired configurations, the outboard region 83 of each side margin 80 of the absorbent composite 32 can be located laterally outboard from a corresponding, terminal side edge 49 of the retention portion 48, and can be located laterally outboard from its corresponding, terminal side edge 81 of the absorbent composite. A further aspect of the invention can include at least one elastomeric member attached approximate to the terminal side edge 81 of each side margin 80 in combination with at least one elastomeric member attached to the outboard region 83 of each side margin 80 of the absorbent composite.

With reference to FIGS. 5A and 5B, each of the leg elastic members 34 can be a composite which includes at least one carrier layer, such as a fabric layer 96, and a plurality of elastomeric strands 98 which are operatively attached to the carrier layer. Various mechanisms, such as adhesive, thermal bonds, sonic bonds, or the like as well as combinations thereof, can be employed to provide the desired attachments between the elastomeric strands 98 and the leg elastic carrier layer 96. In the representatively shown arrangement, each leg elastic member is a laminate composed of a plurality of elastomeric strands sandwiched and held between a pair of carrier layers. Each carrier layer 96 may be composed of a woven or nonwoven fabric having a basis weight within the range of about 10–50 g/m$^2$, but may optionally be composed of a polymer film material. For example, the shown carrier layers may be composed of a polypropylene spunbond nonwoven fabric, and the pair of carrier layers may be adhesively bonded together with a suitable pattern of adhesive, such as a swirl-pattern of pressure-sensitive adhesive.

Where the leg elastic members 34 include a carrier layer or sheet to which are attached a grouped set of elastics composed of a plurality of individual elastic strands, the elastic strands may intersect or be interconnected, or be entirely separated and spaced from each other. The carrier layer may, for example, comprise a 0.002 cm thick polymer film, such as a film of unembossed polypropylene material. The elastic strands can, for example, be composed of LYCRA elastomer available from DuPont, a business having offices in Wilmington, Del. Each elastic strand is typically within the range of about 470–1500 decitex (dtx), and may be about 940–1050 dtx. In particular embodiments of the invention, for example, three or four strands can be employed for each elasticized legband.

As representatively shown in FIG. 5B, the at least one elastomeric member 34 can be a separately provided component attached to the turned bodyside surface 100 of each side margin 80 of the absorbent composite 32, with each elastomeric member 34 including a fabric layer 96 located on a bodyside surface of the elastomeric member 34. Optionally, another fabric layer may also be constructed and arranged to extend along an outward side surface of the elastomeric member. The fabric layers 96 of the elastomeric member 34 can be a knitted fabric, a woven fabric, a non-woven fabric, or the like, as well as combinations thereof. For example, the fabric layer 96 maybe composed of a spunbond fabric (e.g. 1.0 osy polypropylene spunbond), a spunbond-meltblown-spunbond fabric (e.g. 1.0 osy polypropylene spunbond-meltblown-spunbond), a bonded carded web (e.g. 1.0 osy polypropylene bonded carded web) or the like, as well as combinations thereof. The fabric layers 96 can be configured to extend over a selected portion of the turned bodyside surface 100 of each side margin 80 to provide a soft surface for contacting the wearer's body. Alternatively, the fabric layers 96 can extend over substantially the entire, exposed bodyside surface 100 of each side margin 80 of the absorbent composite 32.

Figure 6:
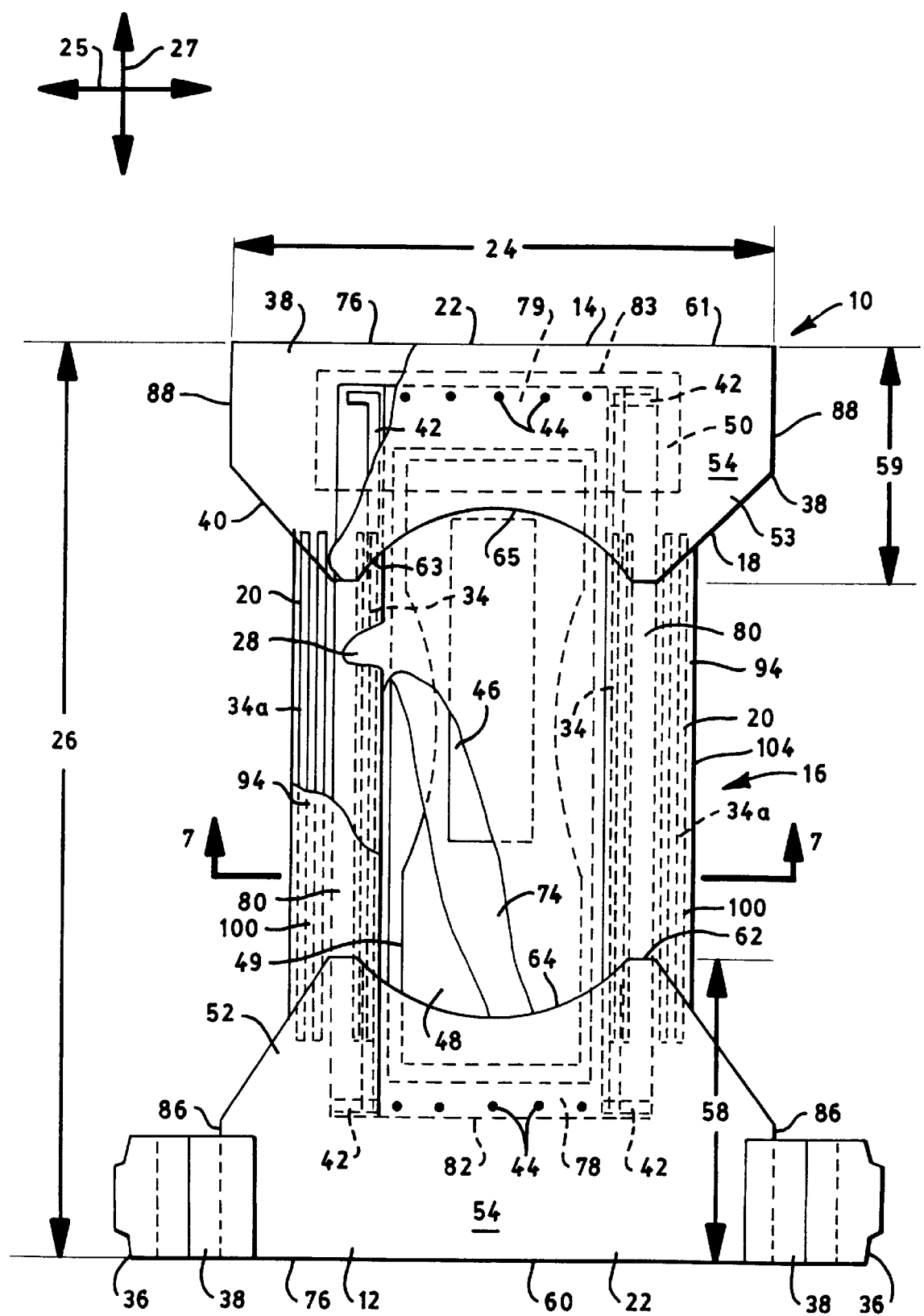
FIG. 6 representatively shows a partially cut-away, plan view of the inner, bodyside surface of an article of the invention which includes another system of leg elastic members joined to the side margins of the absorbent composite.
Figure 7:
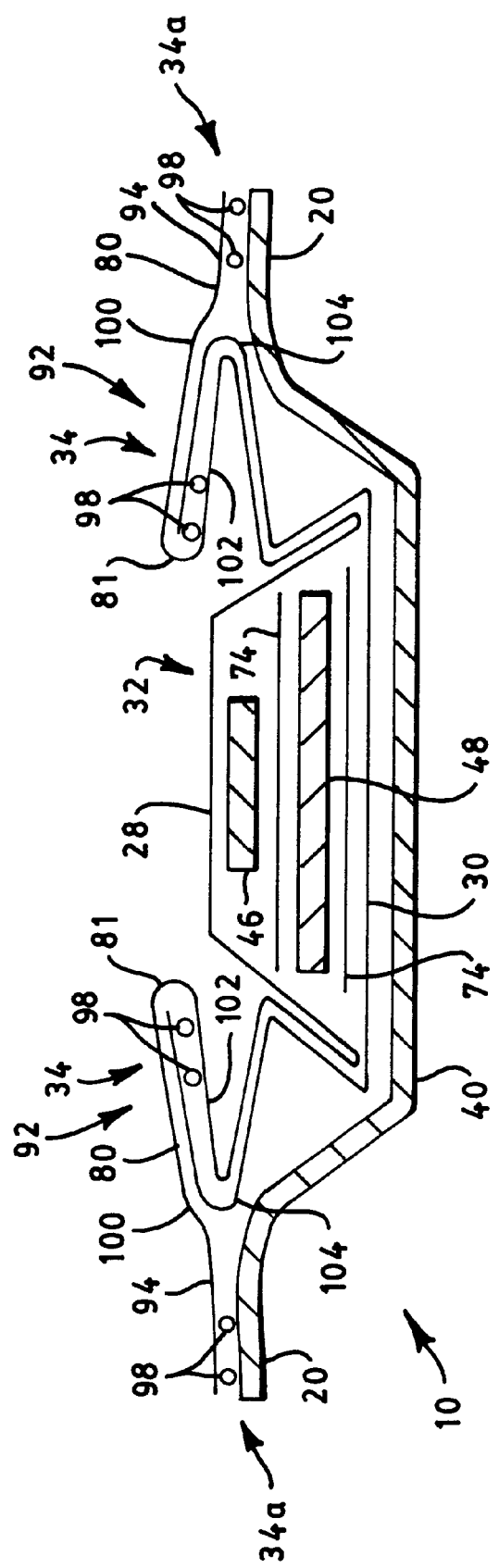
FIG. 7 representatively shows an expanded schematic, lateral cross-sectional view of the article of the invention having the system of elastomeric members joined to the turned-in side margins of the absorbent composite, with respect to line 7—7 of FIG. 6.

FIGS. 6 and 7, representatively show an article having another system of leg elastic members 34. In the illustrated arrangement, a turned-in section of the topsheet layer 28 extends laterally inboard to the terminal side edges of the backsheet 30 along each side margin 80. Each side margin can include a fabric layer (e.g. a portion of topsheet layer 28) which is positioned over the bodyside surface of either or both of the turned-sections of the backsheet layer, and the fabric layer can extend from an area at or adjacent to its associated terminal edge of the backsheet layer, and can extend laterally outboard past its corresponding turning line 104 to provide a side flap 94. Alternatively, each of the side flaps 94 can be provided by a side marginal portion of the extensible outercover layer 40. As representatively shown, each of the side flaps 94 may include terminal side sections of both the appointed fabric layer and the extensible outercover 40. A laterally inboard edge of the fabric layer may terminate at or near its corresponding terminal side edge of the backsheet layer, or may be wrapped around the terminal side edge of the backsheet 30. In the shown configuration, for example, the desired fabric layer is provided by the topsheet layer 28; the topsheet layer wraps around each of the terminal edges of the backsheet layer 30, and extends laterally outward to help form the side flaps 94.

At each lateral side of the article, an appointed elastic section 34a of the leg elastic member 34 can be positioned in its corresponding side flap 94, and can extend longitudinally along the article. As representatively shown, each of the leg elastic sections 34a may include an appointed set of one or more elastomeric strands 98 which are sandwiched between the side marginal portions of the fabric layer and the side marginal portions of the extensible outercover. Additionally, another appointed section of the elastic members 34 can be attached proximate to each terminal side edge region 81 of each side margin 80 of the absorbent composite 32, and can also include one or more elastomeric strands 98.

By employing the selected fabric layer (e.g. topsheet 28) and/or the extensible outer cover 40 to form the side flaps 94, the article can provide a leg gather which substantially excludes the backsheet layer 30. As a result, the leg gather can advantageously form a soft, breathable and conformable gasket.

In the various configurations of the invention, the leg elastics 34 may be generally straight or optionally curved. For example, the curved elastics can be inwardly bowed toward the longitudinal centerline of the diaper. In particular arrangements, the curvature of the elastics may not be configured or positioned symmetrically relative to the lateral centerline of the diaper. The curved elastics may have an inwardly bowed and outwardly bowed, reflex-type of curvature, and the length-wise center of the elastics may optionally be offset by a selected distance toward either the front or rear waistband of the diaper to provide desired fit and appearance. In particular embodiments of the invention, the innermost point (apex) of the set of curved elastics can be offset towards the front or rear waistband of the diaper, and the outwardly bowed reflexed-portion can be positioned toward the diaper front waistband.

The diaper 10 may also include a waist elastic (not shown) positioned in the longitudinal margins of either or both of the front waistband 14 and the rear waistband 12. The waist elastics may be composed of any suitable elastomeric material, such as an elastomer film, an elastic foam, multiple elastic strands, an elastomeric fabric or the like. For example, suitable elastic waist constructions are described in U.S. Pat. No. 4,916,005 to Lippert et al., the entire disclosure of which is hereby incorporated by reference in a manner that is consistent herewith.

With reference to the representative configurations shown in FIGS. 1 and 6, the article may include a system of "ear" regions or ear members 38. In particular arrangements, each ear region or member 38 extends laterally at the opposed, lateral ends of at least one waistband portion of backsheet 30, such as the representatively shown rear waistband portion 12, to provide terminal side sections of the article. In addition, each ear region can substantially span from a laterally extending, terminal waistband edge 76 to approximately the location of its associated and corresponding leg opening section of the diaper. The diaper 10, for example, has a laterally opposed pair of leg openings provided by the curved margins of the ear regions in combination with the correspondingly adjacent, medial sections of the shown pair of longitudinally extending, side edge regions 20 (e.g. FIG. 1). In alternative configurations, the ear regions may be provided by a system of separately provided ear members (not shown).

In the various configurations of the invention, the ear regions may be integrally formed with a selected diaper component. For example, ear regions 38 can be integrally formed from the layer of material which provides backsheet layer 30, or may be integrally formed from the material employed to provide topsheet 28. In alternative configurations, the ear regions 38 may be provided by one or more separately provided members that are connected and assembled to the backsheet 30, to the topsheet 28, in between the backsheet and topsheet, or in various fixedly attached combinations of such assemblies.

In particular configurations of the invention, each of the ear regions 38 may be formed from a separately provided piece of material which is then suitably assembled and attached to the selected front and/or rear waistband portion of the diaper article. For example, each ear region 38 may be attached to the rear waistband portion of the backsheet 30 along an ear region attachment zone, and can be operably attached to either or both of the backsheet and topsheet components of the article. The inboard, attachment zone region of each ear region can be overlapped and laminated with its corresponding, lateral end edge region of the waistband section of the article. The ear regions extend laterally to form a pair of opposed waist-flap sections of the diaper, and are attached with suitable connecting means, such as adhesive bonding, thermal bonding, ultrasonic bonding, clips, staples, sewing or the like. Desirably, the ear regions extend laterally beyond the terminal side edges of the backsheet layer and topsheet layer at the corresponding, attached waistband section of the article.

The ear regions 38 may be composed of a substantially non-elastomeric material, such as polymer films, woven fabrics, nonwoven fabrics or the like, as well as combinations thereof. In particular aspects of the invention, ear regions 38 may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 25. For example, suitable meltblown elastomeric fibrous webs for forming ear regions 38 are described in U.S. Pat. No. 4,663,220 issued May 5, 1987 to T. Wisneski et al., the entire disclosure of which is hereby incorporated by reference. Examples of composite fabrics comprising at least one layer of nonwoven textile fabric secured to a fibrous elastic layer are described in European Patent Application EP 0 217 032 A2 published on Apr. 8, 1987 which has the listed inventors of J. Taylor et al., the entire disclosure of which is hereby incorporated by reference. Examples of NBL materials are described in U.S. Pat. No. 5,226,992 issued Jul. 13, 1993 to Mormon, the entire disclosure of which is hereby incorporated by reference.

As previously mentioned, various suitable constructions can be employed to attach the ear regions 38 to the selected waistband portions of the article. Particular examples of suitable constructions for securing a pair of elastically stretchable members to the lateral, side portions of an article to extend laterally outward beyond the laterally opposed side regions of the outer cover and liner components of an article can be found in U.S. Pat. No. 4,938,753 issued Jul. 3, 1990 to P. VanGompel et al., the entire disclosure of which is hereby incorporated by reference in a manner that is consistent herewith.

Each of the ear regions 38 extends laterally at a one of the opposed lateral ends of at least one waistband section of the diaper 10. In the shown embodiment, for example, a first pair of ear regions extend laterally at the opposed lateral ends of the back waistband section of the backsheet 30, and a second pair of ear regions extend laterally at the opposed lateral ends of the front waistband section of the backsheet. The ear regions can have a tapered, curved or otherwise contoured shape in which the length of its inboard base region is smaller or larger than the length of its relatively outboard end region. The ear regions may, for example, have a substantially rectangular shape or a substantially trapezoidal shape.

Diaper 10 can also include a pair of elasticized containment flaps (not shown) which extend generally length-wise along the longitudinal direction 27 of the diaper. The containment flaps are typically positioned laterally inboard from the leg elastics 34, and substantially symmetrically placed on each side of the lengthwise, longitudinal centerline of the diaper. In the illustrated arrangements, each containment flap has a substantially fixed edge portion and a substantially moveable edge portion, and is operably elasticized with at least one elastomeric member to help each containment flap to closely contact and conform to the contours of the wearer's body. Examples of suitable containment flap constructions are described in U.S. Pat. No. 4,704,116 issued Nov. 3, 1987, to K. Enloe, the entire disclosure of which is hereby incorporated by reference in a manner that is consistent herewith. The containment flaps may be composed of a wettable or a non-wettable material, as desired. In addition, the containment flap material may be substantially liquid-impermeable, may be permeable to only gas or may be permeable to both gas and liquid. Other suitable containment flap configurations are described in U.S. patent application Ser. No. 206,816 of R. Everett et al., filed Mar. 4, 1994 and entitled ABSORBENT ARTICLE HAVING AN IMPROVED SURGE MANAGEMENT (attorney docket No. 11,375), which corresponds to U.S. Pat. No. 5,562,650, the disclosure of which is hereby incorporated by reference in a manner that is consistent herewith.

An extensible outercover 40 may be joined to extend over a major portion of the outward surface of the absorbent composite 32. The extensible outercover is desirably capable of providing a selected elongation when subjected to an applied tensile force. The extensible outercover is also desirably capable of providing a selected, sustained deformation, when subjected to an applied tensile force and then allowed to relax for a selected time period after removing the applied tensile force. The measurement of the selected time period begins immediately after the removal of the tensile force. Desirably, the sustained deformation is a substantially permanent deformation. The selected elongation and sustained deformation can occur at least along the lateral cross-direction 25 of the article. Optionally, the selected elongation and sustained deformation can occur along the longitudinal direction 27 of the article, or may occur along both the cross-direction and longitudinal direction of the article.

In particular aspects, the extensible outercover can provide an elongation of at least about 1 cm when subjected to a tensile force of 30 gmf per inch (per 2.54 cm). The extensible outercover can also provide a substantially permanent deformation of at least about 20%, when subjected to a tensile force of 50 gmf per inch (per 2.54 cm) and then allowed to relax, after a removal of the tensile force, for a period of 1 minute.

In further aspects of the invention, the extensible outercover 40 can be substantially non-elastomeric. Accordingly, the extensible outercover does not have the stretch and retraction characteristics of natural rubber. In other aspects, the absorbent article can include an expandable turned section 92 joined along at least a portion of each side region 80 of the absorbent composite 32 in the first end region 78 and/or second end region 79 of the absorbent composite. Each expandable, turned section 92 can be expandable at least along the cross-direction 25 or at least along an outward direction of said article, and each expandable attachment section is configured to secure its correspondingly joined side edge region of the absorbent composite to the outward surface 56 of its corresponding body panel 52 or 53.

The article of the invention incorporates a distinctive, separately provided extensible outercover 40 which includes an extensible fabric layer which is operatively attached or otherwise joined to extend over a major portion of the outward surface of the article. In particular, the extensible outercover 40 can extend over a major portion of the outward surface of the absorbent composite 32. Desirably, the extensible outercover can extend over substantially an entire area of the outward surface of the absorbent composite. The selected extensibility in the outercover can allow the outercover to accommodate and cooperate with the properties of the other materials or components to which the extensible outercover is attached in the article. In regions where the outercover is not affixed to the article, the extensible outercover can be free to advantageously expand with minimal force and with a high amount of permanent deformation.

Extensible regions in the outercover 40 are provided in areas where the outercover is not directly affixed to the article. In the article of the invention, the extensible regions can desirably be located over the regions of the absorbent composite which are appointed for expansion during the absorption of liquids. For example, the absorbent composite can expand outwardly during use, and the outercover can elongate and extend in correspondence with the expansion of the absorbent composite and/or other components of the article. In desired aspects, the outercover 40 can be extensible along the transverse lateral direction 25. In optional aspects, the outercover can be extensible along the longitudinal direction 27, or along a combination of both the lateral and longitudinal directions.

Elasticized regions in the outercover 40 can be created where the extensible outercover is affixed to an elastomeric component. For example, an elastomeric region in the outercover 40 can be created where the extensible outercover is affixed to an elastomerically stretchable body panel 52. Substantially non-extensible regions in the outercover can be created where the extensible outercover 40 is affixed to a substantially non-extensible component. For example, a substantially non-extensible region in the outercover 40 can be created where the extensible outercover 40 is affixed to a substantially non-extensible component, such as a substantially non-extensible substrate layer (e.g. the topsheet 28 or backsheet 30) of the article.

In particular configurations, the substantially non-extensible regions of the outercover member 40 can be constructed by affixing the extensible nonwoven fabric of the outercover to a substantially non-extensible component, such as a substantially non-extensible backsheet layer 30. With reference to FIG. 2, for example, the resultant non-extensible region can provide a landing zone region 50 which is composed of an integral portion of the nonwoven fabric of the extensible outercover. The backsheet layer 30 of the absorbent composite 32 can, for example, be composed of a substantially non-extensible polymer film, and the nonwoven fabric of the extensible outercover 40 can be adhesively attached or otherwise affixed to the front waistband region of the backsheet layer with a selected outercover attachment, which may be substantially non-extendible. The outercover attachment may be irregularly or randomly distributed, or may be arranged in a predetermined, pattern array, such as the representatively shown swirl patter. The nonwoven fabric can thereby provide a complementary component of an interengaging mechanical fastening system. For example, the affixed portion of the outercover in the landing zone 50 can provide a female loop component of a mechanical hook-and-loop fastening system. The affixing of the extensible outercover material to the polymer film can prevent the necked fabric from excessively elongating and extending in the lateral direction during the ordinary operation of the fastening system.

In particular aspects, the extensible outercover 40 can be capable of providing an elongation of at least a minimum of about 1 cm when subjected to a tensile force of 30 gmf per inch (0.116 Newtons per cm) of cross-wise length ("width") of a test sample. Alternatively, the extensible outercover can provide an elongation of at least about 3 cm, and optionally, can provide an elongation of at least about 5 cm to provide improved performance. In other aspects, the extensible outercover 40 can be capable of providing an elongation of not more than a maximum of about 30 cm when subjected to the tensile force of 30 gmf per inch (0.116 N per cm) of cross-wise length ("width") of a test sample. Alternatively, the extensible outercover can provide an elongation of not more than about 20 cm, and optionally, can provide an elongation of not more than about 10 cm to provide further improved performance.

In further aspects, the extensible outercover can be capable of providing a substantially permanent deformation of at least a minimum of about 20% when subjected to a tensile force of 50 gmf per inch (0.193 Newtons per cm) of cross-wise length of the test sample, and then allowed to relax (after a removal of the applied tensile force) for a period of 1 minute. Alternatively, the extensible outercover can provide a substantially permanent deformation of at least about 20%, and optionally, can provide a substantially permanent deformation of at least about 30% to provide improved benefits. In still other aspects, the extensible outercover can provide a substantially permanent deformation of not more than a minimum of about 60% when subjected to the tensile force of 50 gmf per inch (0.193 N/cm) of cross-wise length of the test sample, and then allowed to relax for a period of 1 minute after a removal of the applied tensile force. Alteratively, the extensible outercover can provide a substantially permanent deformation of not more than about 50%, and optionally, can provide a substantially permanent deformation of not more than about 40% to provide further improved benefits. It should be readily appreciated that the described removal of the applied force results in a zero applied tensile stress and a zero applied tensile force.

It should be noted that the elongation, extension or permanent deformation properties of the outercover are determined when the outercover is dry. Additionally, the percentage of elongation, extension or permanent deformation can be determined in accordance with the following formula: $100*(L-L_o)/(L_o)$;

where: L=elongated length, and
$L_o$=initial length.

The extensible outercover member can be composed of various materials. For example, the extensible outercover can be composed of a necked fabric, a creped fabric, a micro-pleated fabric, polymer films or the like, as well as combinations thereof. The fabrics may be woven or non-woven materials, such as spunbond fabrics.

An example of a suitable extensible outercover material is a 60% necked, polypropylene spunbond having a basis weight of about 1.2 osy. The necked spunbond material had the physical properties representatively shown in the stress-strain curve set forth in U.S. patent application Ser. No. 08/249,434 entitled EXPANDABLE COVER GARMENT by P. T. VanGompel et al. filed Feb. 12, 1999 (attorney docket No. 13,653). The properties of the spunbond material were determined with respect to a 2 inch wide sample having 3 inches of sample length spanning between an initial 3 inch separation of the holding jaws of a conventional set of tensile testing equipment.

Examples of suitable manufacturing techniques and suitable necked nonwoven fabric materials are described in U.S. Pat. No. 4,965,122 entitled REVERSIBLE NECKED MATERIAL AND PROCESS TO MAKE IT, by M. T. Morman which was issued Oct. 23, 1990. The entire disclosure of this document is incorporated herein by reference in a manner that is consistent herewith.

For the purposes of the present disclosure, the term "% necked" or "percent neckdown" refers to a ratio or percentage determined by measuring the difference between the pre-necked dimension and the necked dimension of a neckable material, and then dividing that difference by the pre-necked dimension of the neckable material. The percentage of necking (percent neck) can be determined in accordance with the description in the above-mentioned U.S. Pat. No. 4,965,122 entitled REVERSIBLE NECKED MATERIAL AND PROCESS TO MAKE IT, by M. T. Morman which was issued Oct. 23, 1990.

The necked nonwoven fabric can be configured to be substantially non-extensible in a selected region of the outercover member 40. For example, the necked nonwoven fabric be employed to construct an improved fastener landing zone 50 which includes the necked spunbond fabric layer. More particularly, the backsheet layer 30 of the absorbent composite 32 can be composed of a substantially non-extensible polymer film, and the necked spunbond fabric of the extensible outercover 40 can be adhesively attached to the front waistband region of the backsheet layer. The necked spunbond fabric can thereby provide the appointed, female loop component of a mechanical hookand-loop fastening system, wherein the adhesive attachment to the non-extensible polymer film can prevent the necked spunbond from laterally elongating and extending during the ordinary operation of the fastening system.

The necked spunbond fabric can also provide a very cloth-like feel to the outercover 40. The necked fabric is desirably air-permeable, and breathability regions can be created where the extensible outercover material is attached to overlie a breathable component which is positioned on the bodyside of the outercover. For example, the extensible cover 40 can be attached to overlie a front body panel 52 composed of an air-permeable SMS (spunbond-meltblown-spunbond) laminate material. Since the SMS front body panel and the attached, necked spunbond fabric are both breathable, the overall composite of the necked spunbond and SMS materials can remain breathable.

As representatively shown, the front waistband section 14 of the diaper 10 has a laterally opposed, front pair of side edge regions 88, and the rear waistband section 12 has a laterally opposed, rear pair of side edge regions 86. The intermediate section 16 interconnects the front and rear waistband section and provides a diaper crotch region which is typically positioned between the legs of the wearer. The article has an appointed fastener landing member 50 which is disposed on the outward surface of the article. In the example representatively shown in FIG. 3, for example, the landing member 50 can be disposed on the outward surface of the backsheet layer 30. The liquid permeable topsheet layer 28 is superposed in facing relation with the backsheet layer 30, and the retention portion 48 is operably connected and affixed between the backsheet layer 30 and topsheet layer 28. In desired arrangements, the topsheet layer 28 and the retention portion 48 can be constructed to be substantially nonelastomeric and can be operatively attached to the backsheet member 30 to substantially restrain excessive stretching of the backsheet member.

Examples of articles having extensible outercovers and absorbent composites with expandable side margins are described in U.S. patent application Ser. No. 09/249,434 entitled EXPANDABLE COVER GARMENT by P. T. VanGompel et al. filed Feb. 12, 1999 (attorney docket No. 13,653); and U.S. patent application Ser. No. 09/250,470 entitled A DISPOSABLE GARMENT HAVING DRYNESS BARRIERS WITH EXPANDABLE ATTACHMENT TO AN ABSORBENT by P. T. VanGompel et al. filed Feb. 12, 1999 U.S. Pat. No. 6,132,410 (attorney docket No. 13,612). The entire disclosures of these documents are incorporated herein by reference in a manner that is consistent herewith.

To provide a desired refastenable fastening system, the diaper 10 can include one or more appointed landing zone regions, such as a first, primary landing zone 50 (e.g. FIGS. 2 and 3), which can provide an operable target area for receiving a releasable and re-attachable securement of the fastener tabs 36 thereon. In particular embodiments of the invention, the landing zone patch can be positioned on the front waistband portion 14 of the diaper and is located on the outward surface of the backsheet layer 30. Alternatively, the landing zone patch can be positioned at the rear waistband portion 12 of the article, or optionally may be disposed on an appointed inward surface of the article, such as the bodyside surface of the topsheet layer 28. The fastening mechanism between the landing zone and the fastener tabs 36 may be adhesive, cohesive, mechanical or combinations thereof. In the context of the present invention, a mechanical fastening system is a system which includes cooperating components which mechanically inter-engage to provide a desired securement.

The mechanical fastener components can be provided by mechanical-type fasteners such as hooks, buckles, snaps, buttons and the like, which include cooperating and complementary, mechanically interlocking components. For example, the mechanical fastening system may be a hook-and-loop type of fastening system. Such fastening systems generally comprise a "hook" or hook-like, male component, and a cooperating "loop" or loop-like, female component which engages and releasably interconnects with the hook component. Desirably, the interconnection is selectively releasable and re-attachable over several cycles. Conventional systems are, for example, available under the VEL-CRO trademark. The elements of the hook component may be provided by a single or multiple hook configuration, such as provided by a mushroom-head type of hook element. The elements of the loop component may be provided by a woven fabric, a nonwoven fabric, a knitted fabric, a perforated or apertured layer, and the like, as well as combinations thereof. The many arrangements and variations of such fastener systems have been collectively referred to as hook-and-loop fasteners.

Figure 1D:
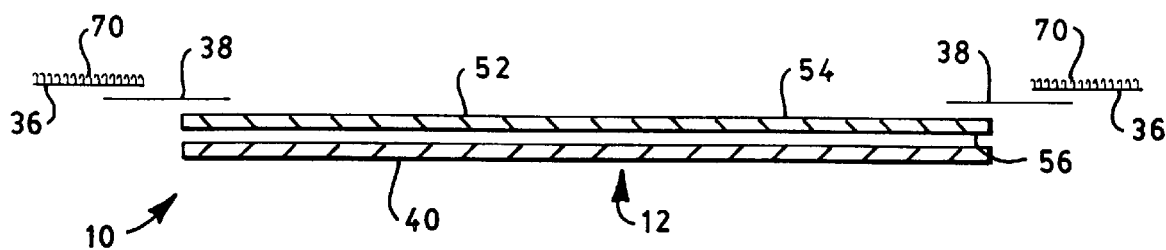
FIG. 1D representatively shows an expanded schematic, lateral cross-sectional view taken with respect to line D—D of FIG. 1.

A configuration which employs a releasable, interengaging mechanical fastening system can, for example, locate the first component of the mechanical fastener, such as a hook material 70 (FIG. 1D), on the fastener tab 36 and a second, cooperating component of the mechanical fastener, such as a loop material 72 (FIG. 3), on the landing zone 50. It should also be readily apparent that, in the various configurations of the invention, the relative positions and/or materials of the fastening component and its corresponding landing zone component can be transposed. Accordingly, the first component of the mechanical fastener can be located on the landing zone 50 and the second, cooperating component of the mechanical fastener can be located on the fastener tab 36.

Examples of suitable hook-and-loop fastening systems are described in U.S. Pat. No. 5,019,073 issued May 28, 1991 to T. Roessler et al., the entire disclosure of which is hereby incorporated by reference in a manner that is consistent herewith. Other examples of hook-and-loop fastening systems are described in U.S. patent application Ser. No. 366,080 entitled HIGH-PEEL TAB FASTENER, filed Dec. 28, 1994 by G. Zehner et al. (attorney docket No. 11,571) which issued as U.S. Pat. No. 5,605,735; and U.S. patent application Ser. No. 421,640 entitled MULTI-ATTACHMENT FASTENING SYSTEM, filed Apr. 13, 1995 by P. VanGompel et al.; the entire disclosures of which are hereby incorporated by reference in a manner that is consistent herewith. Examples of fastening tabs constructed with a carrier layer are described in U.S. Pat. No. 08/603,477 of A. Long et al., entitled MECHANICAL FASTENING SYSTEM WITH GRIP TAB and filed Mar. 6, 1996 (attorney docket No. 12,563), now U.S. Pat. No. 5,624,429 issued Apr. 29, 1997, the entire disclosure of which is hereby incorporated by reference in a manner which is consistent herewith.

In the various embodiments of the invention, a separately provided tape fastener tab 36 can be located at either or both of lateral end regions 86 and 88 of either or both of the waistbands 14 and 12, respectively. The representatively shown embodiment, for example, has at least one of the fastener tabs 36 located at each of the distal side edges of the rear waistband 12. More particularly, each of the fasteners 36 is assembled and attached to extend from a corresponding, immediately adjacent ear region provided at one of the laterally opposed, distal ends of the first body panel 52.

In the shown hook-and-loop fastening system, the hook material is operably connected to the fastening tab 36, and the loop material is employed to construct at least one cooperating landing zone 50. The landing zone may, for example, be disposed on the outward surface of the backsheet 30. As representatively shown, the landing zone can be suitably positioned on the exposed, outward-side surface of the second, front body panel 53. An alternative configuration of the hook-and-loop fastening system may have the loop material secured to the fastener tab 36 and the hook material employed to form the landing zone 50. Each appointed landing zone may be a separately provided member assembled to the appropriate body panel 52 or 53, or may be integrally formed with the body panel. For example, the outward surface of the body panel 53 may be composed of a fabric that provides an operative loop material for the fastening system.

In the various aspects and configurations of the invention, the hook element material can be of the type referred to as micro-hook material. A suitable micro-hook material is distributed under the designation CS200 and is available from 3M Company, a business having offices in St. Paul, Minn. The micro-hook material can have hooks in the shape of mushroom "caps", and can be configured with a hook density of about 1600 hooks per square inch; a hook height which is within the range of about 0.033–0.097 cm (about 0.013 to 0.038 inch); and a cap width which is within the range of about 0.025–0.033 cm (about 0.01 to 0.013 inch). The hooks are attached to a base film substrate having a thickness of about 0.0076–0.01 cm (about 0.003–0.004 inch) and a Gurley stiffness of about 15 mgf.

Another suitable micro-hook material is distributed under the designation VELCRO CFM-29 1058, and is available from VELCRO U.S.A., Inc., a business having offices in Manchester, N.H. The micro-hook material can have hooks in the shape of angled hook elements, and can be configured with a hook density of about 264 hooks per square centimeter (about 1700 hooks per square inch); a hook height which is within the range of about 0.030–0.063 cm (about 0.012–0.025 inch); and a hook width which is within the range of about 0.007 to 0.022 cm (about 0.003 to 0.009 inch). The hook elements are coextruded with a base layer substrate having a thickness of about 0.0076–0.008 cm (about 0.003–0.0035 inch), and the member of hook material has a Gurley stiffness of about 12 mgf (about 12 Gurley units).

For the purposes of the present invention, the various stiffness values are determined with respect to a bending moment produced by a force which is directed perpendicular to the plane substantially defined by the length and width of the component being tested. A suitable technique for determining the stiffness values described herein is a Gurley Stiffness test, a description of which is set forth in TAPPI Standard Test T 543 om-94 (Bending Resistance of Paper (Gurley type tester)). A suitable testing apparatus is a Gurley Digital Stiffness Tester; Model 4171-D manufactured by Teledyne Gurley, a business having offices in Troy, N.Y. For purposes of the present description, the stated Gurley stiffness values are intended to correspond to the values that would be generated by a "standard" sized sample. Accordingly, the scale readings from the Gurley stiffness tester are appropriately converted to the stiffness of a standard size sample, and are traditionally reported in terms of milligrams of force (mgf). Currently, a standard "Gurley unit" is equal to a stiffness value of 1 mgf, and may equivalently be employed to report the Gurley stiffness.

In the various aspects and configurations of the invention, the loop material can be provided by a nonwoven, woven or knit fabric. For example, a suitable loop material fabric can be composed of a 2 bar, warp knit fabric of the type available from Guilford Mills, Inc., Greensboro, N.C. under the trade designation #34285, as well other of knit fabrics. Suitable loop materials are also available from the 3M Company, which has distributed a nylon woven loop under their SCOTCH MATE brand. The 3M Company has also distributed a liner-less loop web with adhesive on the backside of the web, and 3M knitted loop tape.

In particular aspects of the invention, the loop material need not be limited to a discrete landing zone patch. Instead the loop material can, for example, be provided by a substantially continuous, outer fibrous layer which is integrated to extend over substantially the total exposed surface area of a cloth-like outer cover employed with the diaper 10. The resultant, cloth-like backsheet 30 can thereby provide the loop material for an operative "fasten anywhere" mechanical fastening system.

In the various configurations of the invention, the engagement force between the particular fastening component and its appointed landing zone component should be large enough and durable enough to provide an adequate securement of the article on the wearer during use.

Each of the fastening components and elements in the various constructions of the invention may be operably attached to its supporting substrate by employing any one or more of the attachment mechanisms employed to construct and hold together the various other components of the article of the invention. The fastening elements in the various fastening regions, may be integrally formed, such as by molding, co-extrusion or the like, along with the associated substrate layer. The substrate layer and its associated mechanical fastening elements may be formed from substantially the same polymer material, and there need not be a discrete step of attaching the fastening elements to an initially separate substrate layer. For example, the individual hook elements may be integrally formed simultaneously with a hook base-layer by coextruding the base layer and hook elements from substantially the same polymer material.

It should be readily appreciated that the strength of the attachment or other interconnection between the substrate layer and the attached fastening component should be greater than the peak force required to remove the fastener tab 36 from its releasable securement to the appointed landing zone of the article.

EXAMPLE

The following example is presented to provide a more detailed understanding of the invention. The example is representative, and are not intended to limit the scope of the invention.

A representative example of the invention provided a size 3 or medium size diaper for an infant weighting between 16 to 28 pounds. The diaper had the configurations and shapes illustrated in FIGS. 1 through 1C.

The front (second) body panel 53 measured 1 inches along the cross-direction and 4.5 inches along the longitudinal direction, and was composed of a 1.0 osy (28 g/m$^2$) polypropylene spunbond fabric. The back (first) body panel 52 measured 11 inches along the cross-direction and 5.75 inches along the longitudinal direction, and was made of a necked-bonded-laminate material which had a basis weight of 77 g/m$^2$ and was laterally stretchable 20–40% in the cross-direction. The desired curvatures were formed along the medial portions of the inboard edges 64 and 65 of the back and back panels 52 and 53, respectively. Four, 0.25 inch wide strips of 3M-927 two-sided adhesive tape were applied to attach the turned sections 92 of the absorbent composite to the front and back panels at the four side securement sections 42.

The absorbent body composite 32 included a substantially liquid-impervious backsheet layer 30 which measured 8 inches along the cross-direction and 14 inches in the longitudinal direction, and was composed of a 0.75 mil thickness, polyethylene film. A cellulose tissue wrap sheet 74 was overlaid onto and wrapped around a retention portion 48 that was composed of a mixture of 63% cellulosic, woodpulp fluff and 37% superabsorbent polymer (FAVOR 880 from Stockhausen). The wrapped retention portion was debulked to a thickness of 0.2 inch, and cut to an hourglass shape. The shaped retention portion measured 12 inches in the longitudinal direction, and had a narrowed crotch which measured 3.5 inches in the cross-direction. The two, longitudinally opposed ends of the retention portion measured about 4 inches in the cross-direction. A layer of surge material 46 was adhesively attached to the front of the tissue wrap at a location spaced about 2 inches from the front-most edge of the tissue wrap. The surge layer had a basis weight of 2.5 osy and a density of 0.024 g/cc, and measured 3 inches in the cross-direction and 6 inches in the longitudinal direction. A light spray of adhesive was applied to the backsheet layer to attach the backsheet layer to the tissue wrapped retention portion. The front-most edge of the tissue wrap sheet was placed about 0.75 inboard from the leading, front-most edge of the backsheet layer, and a light spray of adhesive attached the top, bodyside surface of the surge layer 46 to the outward surface of the liquid-permeable topsheet layer 28. The topsheet was composed of a 0.5 osy polypropylene spunbond fabric treated with 0.3% surfactant, and was placed over the surge layer 46, the wrapsheet 74 and the retention portion 48. The topsheet was adhesively bonded to the various absorbent components and to the perimeter of backsheet layer to create the assembled, absorbent body composite.

The side edge regions 80 of the topsheet and backsheet layers in the absorbent body composite 32 were folded and tucked to create the C-turned portions 92. The inward-facing, topsheet portion of the C-turned portions 92 was then attached to the outward-fading surfaces of the front and back panels with 0.25 wide strips of adhesive located at the four side securement sections 42. Accordingly the absorbent body composite 32 assembled and joined to interconnect and bridge between the spaced-apart front body panel 53 and back body panel 52.

Each leg elastic member 34 included two, 940 dtx elastomeric strands 98 composed of LYCRA XA SPANDEX. The elastomeric strands were elongated to a 300% elongation and adhesively laminated to a 0.4 osy polypropylene spunbond facing member 96 with a Findley adhesive H2525A. The leg elastic member was stretched-to-stop, and ultrasonically point-bonded to the side marginal edges of the backsheet 30. In particular, the elastic members were located on the outward facing surface of the backsheet layer and positioned within a fold-region of the C-turned portions 92. Longitudinal end portions of each leg elastic member 34 were angled outboard to extend laterally beyond the side edge regions 80 of the absorbent composite, and were attached to the front and back body panels. Accordingly, the laterally opposed pair of leg elastic members 34 created a gathered element at each leg opening of the diaper.

Mechanical, hook-type fastener tabs 36 were adhesively and ultrasonically bonded to the ear portions 38 of the back body panel 52 of the diaper. Preferably, the longitudinally terminal edges of the fastener tabs were substantially aligned with the end edge 60 of the back body panel 52 at the waist band side edge regions 86.

The landing zone patch 50 was composed of a 0.5 osy polypropylene spunbond fabric, which was necked 60% and cut to measure 3 inches in the longitudinal direction and 11 inches along the cross-direction. The landing zone patch was sprayed with adhesive and attached along the outboard edge 61 of the front panel 53 to overlap the front end region 79 of the absorbent body composite 32. End attachments 44 composed of sonic bonds affixed the terminal end edge regions of the absorbent composite to the front and back panels.

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. An integral absorbent article having a longitudinal article length and a lateral article width, said article comprising:
    an absorbent composite having first and second longitudinally opposed end regions,
        and at least a first, longitudinally terminal, end edge,
            said absorbent composite including
            a substantially liquid-impermeable backsheet layer,
            a substantially liquid permeable topsheet layer, and
            a retention portion sandwiched between said backsheet and topsheet layers,
            said retention portion having laterally opposed, terminal side edges, and
            said absorbent composite including a pair of laterally opposed side margins which extend laterally beyond said side edges of said retention portion; and
    a first body panel joined to said first longitudinal end of said absorbent composite, said
        first body panel having
        a bodyside surface,
        an outward surface,
        a panel length which is less than said article length,
        an outboard terminal end edge, and
        a relatively inboard terminal end edge; wherein
    each of said side margins of said absorbent composite is inwardly turned to provide a turned bodyside surface and a turned outward side surface of each side margin, and
    at least a first portion of said turned bodyside surface of each side margin of said absorbent composite is secured to said outward surface of said first body panel.

2. An absorbent article as recited in claim 1, wherein each of said side margins of said absorbent composite is inwardly, C-turned to provide said turned bodyside surface and said turned outward side surface of each said side margin.

3. An absorbent article as recited in claim 1, wherein at least one of said topsheet and backsheet layers extends laterally beyond said side edges of said retention portion to provide said laterally opposed, side margins of said absorbent composite.

4. An absorbent article as recited in claim 1, wherein said first, outboard terminal end edge of said first body panel is substantially coterminous with a first terminal end edge of said article.

5. An absorbent article as recited in claim 1, wherein at least a medial portion of said inboard end edge of said first body panel is substantially unattached to said absorbent composite.

6. An absorbent article as recited in claim 1, wherein said first longitudinally terminal end edge of the absorbent composite is spaced relatively inboard from said outboard terminal end edge of the first body panel.

7. An absorbent article as recited in claim 1, further including at least one elastomeric member attached proximate to a terminal, side edge of each said side margin of the absorbent composite.

8. An absorbent article as recited in claim 7, further including at least one elastomeric member attached to an outboard region of each said side margin of said absorbent composite.

9. An absorbent article as recited in claim 1, further including at least one elastomeric member attached to said turned bodyside surface of each said side margin of the absorbent composite, each said elastomeric member including a fabric layer located on a bodyside surface of said elastomeric member.

10. An absorbent article as recited in claim 9, wherein said outboard region of each said side margin of the absorbent composite is located laterally outboard from a corresponding terminal side edge of said retention portion.

11. An absorbent article as recited in claim 1, wherein said side margins of said absorbent composite are inwardly turned along corresponding turning lines which are substantially parallel to each other.

12. An absorbent article as recited in claim 1, wherein said side margins of said absorbent composite are inwardly turned along corresponding turning lines which are substantially non-parallel to each other.

13. An absorbent article as recited in claim 1, wherein said side margins of said absorbent composite are inwardly turned along corresponding turning lines which are substantially non-parallel to each other, and said turning lines are relatively further apart from each other at said first longitudinal end region of said absorbent composite.

14. An absorbent article as recited in claim 1, wherein a first laterally extending end seal is provided along at least a portion of said first end region of the absorbent composite to resist a passage of liquid between said absorbent composite and said outward surface of said first body panel.

15. An absorbent article as recited in claim 1, wherein said first body panel includes an elastomeric material which is elastomerically stretchable at least along said lateral article width.

16. An absorbent article as recited in claim 1, wherein said first body panel has a longitudinal length which is at least about 5% of said article length.

17. An absorbent article as recited in claim 1, further comprising a separately provided second body panel joined to said second end region of the absorbent composite, wherein said second body panel has a panel length which is less than said article length, and at least a second portion of said turned bodyside surface of each side margin of said absorbent composite is secured to an outward surface of said second body panel with a corresponding body panel attachment.

18. An absorbent article as recited in claim 17, wherein said second body panel is longitudinally spaced from said first body panel.

19. An absorbent article as recited in claim 17, wherein said second body panel has an outboard terminal end edge which is substantially coterminous with a second end edge of said article.

20. An absorbent article as recited in claim 17, wherein said second body panel has an inboard terminal end edge, at least a medial portion of which is substantially unattached to said absorbent composite.

21. An absorbent article as recited in claim 17, further comprising an expandable attachment section joined along at least a portion of each side region of the absorbent composite in said second end region of the absorbent composite, each expandable attachment section expandable at least outwardly, and each expandable attachment section configured to secure its correspondingly joined side edge region of the absorbent composite to said outward surface of said second body panel.

22. An absorbent article as recited in claim 17, wherein said second body panel has a longitudinal length which is not more than about 40% of said article length.

23. An absorbent article as recited in claim 17, wherein said second body panel has a longitudinal length which is at least about 5% of said article length.

* * * * *

UNITED STATES PATENT AND TRADEMARK OFFICE
CERTIFICATE OF CORRECTION

PATENT NO. : 6,217,563 B1
DATED : April 17, 2001
INVENTOR(S) : Paul Theodore Van Gompel et al.

Page 1 of 1

It is certified that error appears in the above-identified patent and that said Letters Patent is hereby corrected as shown below:

Title page,
Item [56], References Cited,
FOREIGN PATENT DOCUMENTS, delete "2 068 316 A1", and substitute
-- 2 680 316 A1 --.

Column 25,
Line 29, delete "patter", and substitute -- pattern --.

Column 30,
Line 56, delete "1;", and substitute -- 11 --.

Column 31,
Line 42, delete "outward-fading", and substitute -- outward-facing --.

Signed and Sealed this

Twelfth Day of March, 2002

*Attest:*

*Attesting Officer*

JAMES E. ROGAN
*Director of the United States Patent and Trademark Office*